United States Patent
Kreider et al.

(10) Patent No.: US 10,689,333 B1
(45) Date of Patent: Jun. 23, 2020

(54) 2-MERCAPTOETHANOL SYNTHESIS

(71) Applicant: Chevron Phillips Chemical Company LP, The Woodlands, TX (US)

(72) Inventors: Jason L. Kreider, Copan, OK (US); Daniel M. Hasenberg, Kingwood, TX (US); Alex Pauwels, Deurne (BE)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 16/282,769

(22) Filed: Feb. 22, 2019

(51) Int. Cl.
*C07C 319/02* (2006.01)
*B01J 29/08* (2006.01)

(52) U.S. Cl.
CPC ........... *C07C 319/02* (2013.01); *B01J 29/084* (2013.01)

(58) Field of Classification Search
CPC .............................. C07C 319/02; B01J 29/084
See application file for complete search history.

(56) References Cited

U.S. PATENT DOCUMENTS

| | | | |
|---|---|---|---|
| 2,776,997 A | 1/1957 | Doumani | |
| 3,086,997 A | 4/1963 | Warner | |
| 3,290,383 A | 12/1966 | Pflugfelder et al. | |
| 3,366,693 A | 1/1968 | Randall et al. | |
| 3,394,192 A | 7/1968 | Jones | |
| 3,462,496 A | 8/1969 | Fletcher et al. | |
| 3,574,768 A | 4/1971 | Tompkins | |
| 3,662,004 A | 5/1972 | Umbach et al. | |
| 3,710,439 A | 1/1973 | Goetze et al. | |
| 4,083,876 A | 4/1978 | Bruns et al. | |
| 4,281,202 A | 7/1981 | Buchholz et al. | |
| 4,398,042 A | 8/1983 | Kleenmann et al. | |
| 4,493,938 A | 1/1985 | Shimamoto et al. | |
| 4,507,505 A | 3/1985 | Arretz | |
| 4,564,710 A | 1/1986 | Steger | |
| 4,985,586 A | 1/1991 | Arretz et al. | |
| 7,399,893 B2 | 7/2008 | Hasenberg et al. | |
| 7,645,906 B2 | 1/2010 | Hasenberg et al. | |
| 9,718,767 B2 | 8/2017 | Hasenberg et al. | |

(Continued)

FOREIGN PATENT DOCUMENTS

| | | |
|---|---|---|
| CN | 101941928 | 1/2011 |
| DE | 2129162 | 12/1971 |

(Continued)

OTHER PUBLICATIONS

A A Malievsky, "Synthesis of mercaptans and sulfides in the liquid phase reaction of hydrogen sulfide with alkylene oxides assessment of catalysts effectiveness", 2012, Kataliz v Promyshiennosti, Issue 6, pp. 23-32.*

(Continued)

*Primary Examiner* — Rosalynd A Keys
(74) *Attorney, Agent, or Firm* — Conley Rose, P.C.

(57) ABSTRACT

A process comprising reacting, in a reactor having a fixed bed containing a solid catalyst which contains a zeolite, hydrogen sulfide and an oxirane in the presence of the solid catalyst to yield a reaction product with contains a mercapto-alcohol. A reactor system includes the reactor, an oxirane feed stream, a hydrogen sulfide feed stream, a fixed bed containing the solid catalyst placed inside the reactor, and an effluent stream containing the reaction product. The hydrogen sulfide and the oxirane are present in a mole ratio in a range of about 5:1 to 50:1.

37 Claims, 5 Drawing Sheets

(56) References Cited

U.S. PATENT DOCUMENTS

2014/0179881 A1* 6/2014 McDaniel ................ B01J 8/082
  526/64
2017/0291873 A1 10/2017 Hasenberg et al.

FOREIGN PATENT DOCUMENTS

| EP | 0039062 | 11/1981 |
| EP | 1923384 | 5/2008 |
| GB | 988135 | 4/1965 |
| GB | 1296452 | 11/1972 |
| GB | 585655 | 2/1974 |
| GB | 2077263 | 12/1981 |
| JP | 60058932 | 4/1985 |
| JP | 2006184251 | 7/2006 |
| JP | 2008013453 | 1/2008 |
| RU | 2556859 | 7/2018 |

OTHER PUBLICATIONS

A A Malievsky, "Synthesis of mercaptans and sulfides in the liquid phase reaction of hydrogen sulfide with alkylene oxides assessment of catalysts effectiveness", 2012, Kataliz v Promyshiennosti, Issue 6, partial English translation of p. 25.*
McNaught, Alan D., et al. "Compendium of Chemical Terminology." IUPAC Recommendations, Second Edition, 1997, 5 pages, Wiley-Blackwell.

* cited by examiner

US 10,689,333 B1

2-MERCAPTOETHANOL SYNTHESIS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD

The present disclosure relates to the synthesis of hydroxy-mercaptans via the conversion of oxiranes.

BACKGROUND

Beta-mercaptoethanol (BME) is mainly used in poly(vinyl chloride) (PVC) production as an intermediate for the synthesis of PVC heat stabilizers and as a process regulator in PVC manufacturing. BME is a common reducing agent and is also used as a component in corrosion inhibitors, as a processing aid for the leather industry, and as a laboratory chemical in biochemical applications. BME is generally produced via reaction of ethylene oxide (EO) with hydrogen sulfide ($H_2S$) in a continuous stirred-tank reactor (CSTR) in the presence of excess hydrogen sulfide ($H_2S$). The industry specification for BME is typically 99.0% BME or greater; however, in a CSTR, conversion of ethylene oxide to BME is limited, and undesirable side products such as thiodiglycol and other heavy products are also produced. Thus, there is an ongoing need for developing methods for producing BME, particularly high-purity BME.

SUMMARY

Disclosed is a process comprising reacting, in a reactor having a fixed bed containing a solid catalyst comprising a zeolite, hydrogen sulfide, and an oxirane compound in the presence of the solid catalyst to yield a reaction product comprising a mercapto-alcohol.

DETAILED DESCRIPTION

Overview

Figure 1:
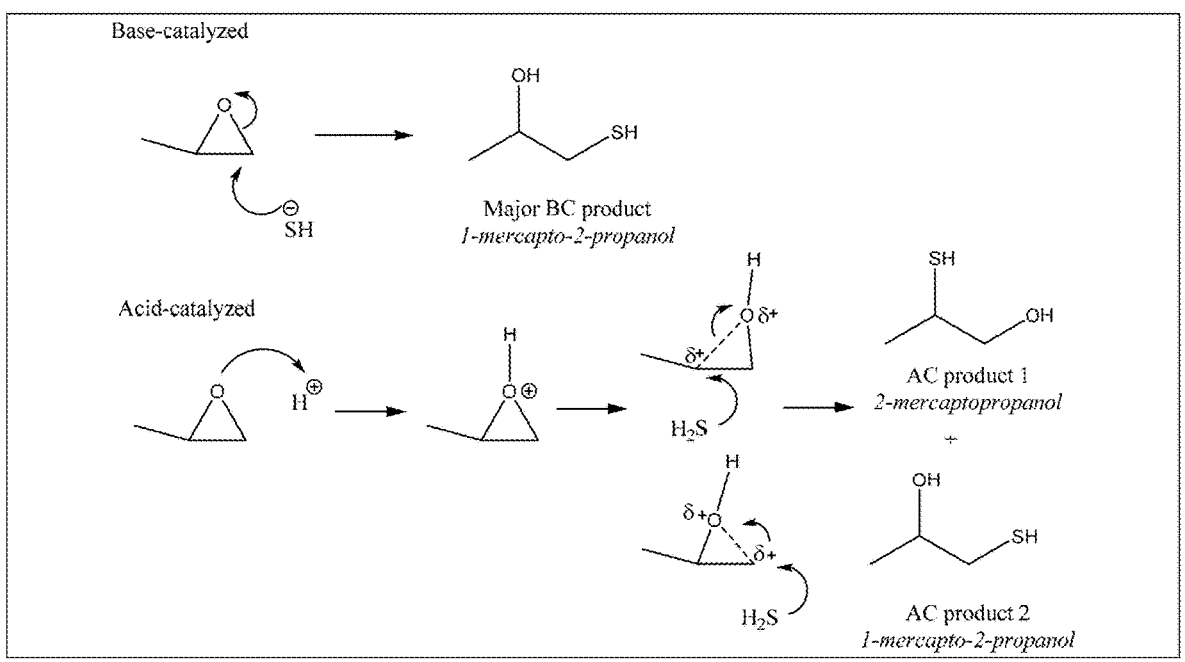
FIG. 1 shows proposed chemical mechanisms for reaction of propylene oxide and hydrogen sulfide.

Disclosed herein are aspects of processes to produce a sulfur-containing reaction product via reaction of a reactant in an excess of hydrogen sulfide ($H_2S$) and in the presence of a solid catalyst. In a particular aspect, the sulfur-containing reaction product can be an unsubstituted hydroxymercaptan (e.g., 2-mercapto-1-ethanol also referred to as BME, CAS Number 60-24-2), a substituted hydroxymercaptan (e.g., 1-mercapto-2-propanol, 2-mercapto-1-propanol), or a combination thereof, and the reactant can be an oxirane (e.g., ethylene oxide, propylene oxide). In an aspect, the oxirane can react with $H_2S$ in a reactor with a fixed bed containing a solid catalyst comprising a zeolite. In some aspects, the zeolite can have acidic active groups to allow for conversion of the oxirane by $H_2S$.

Definitions

The following definitions are provided in order to aid those skilled in the art in understanding the detailed description of the present disclosure. Unless otherwise defined herein, scientific and technical terms used in connection with the present disclosure shall have the meanings that are commonly understood by those of ordinary skill in the art to which this disclosure belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

As used herein, β-mercaptoethanol (BME) can also be referred to by various synonyms including, but not limited to, 2-sulfanylethanol (IUPAC name), 2-hydroxy-1-ethanethiol, thioglycol, 2-mercaptoethanol, 2-mercapto-1-ethanol, 2-thioethanol, 2-hydroxyethyl mercaptan, and others.

As used herein, ethanedithiol can also be referred to by various synonyms, including, but not limited to, ethane-1,2-dithiol (IUPAC name), 1,2-ethanedithiol, 1,2-dimercaptoethane, dithioglycol, ethylene mercaptan, and others.

As used herein, thiodiglycol can also be referred to by various synonyms including, but not limited to, 2-(2-hydroxyethylsulfanyl) ethanol (IUPAC name), 2,2'-thiodiethanol, thiodiethanol, thiodiethylene glycol, and others.

As used herein, hydroxymercaptan refers to a broad class of compounds comprising a mercaptan (i.e., thiol) containing a hydroxyl (—OH) functional group. Examples of hydroxymercaptans include 2-mercapto-1-ethanol, 1-mercapto-2-propanol, and 2-mercapto-1-propanol.

As used herein, oxirane refers to a saturated hydrocarbon comprising a three-membered ring wherein the ring contains a single oxygen atom. Oxiranes are also referred to as epoxides or cyclic ethers. A non-functionalized oxirane may also be termed ethylene oxide.

As used herein, oxetane refers to a saturated hydrocarbon comprising a four-membered ring wherein the ring contains a single oxygen atom. Oxetanes are also referred to as cyclic ethers.

As used herein, thiirane refers to a saturated hydrocarbon comprising a three-membered ring wherein the ring contains a single sulfur atom. Thiiranes are also referred to as cyclic thioethers. A non-functionalized thiirane may be called ethylene sulfide.

As used herein, thietane refers to a saturated hydrocarbon comprising a four-membered ring wherein the ring contains a single sulfur atom. Thietanes are also referred to as cyclic thioethers.

Although any methods, devices, and materials similar or equivalent to those described herein can be used in the practice or testing of the present disclosure, the typical methods, devices, and materials are herein described.

Scope of Reactants and Reaction Products

In an aspect, a process for producing a sulfur-containing reaction product includes reacting hydrogen sulfide ($H_2S$) and a reactant in a reactor with a fixed bed solid catalyst comprising a zeolite. In a particular aspect, a process for producing a hydroxymercaptan can comprise reacting, in a reactor having a fixed bed containing a solid catalyst comprising a zeolite, hydrogen sulfide ($H_2S$), and an oxirane (e.g., ethylene oxide, propylene oxide), in the presence of the solid catalyst to yield the hydroxymercaptan. The production of BME via reaction of ethylene oxide and $H_2S$ is a commercially important chemical process, and thus the production of BME is used repeatedly throughout this description as a non-limiting example of a specific process.

In an aspect, the reactant comprises an olefin, a cyclic ether, a cyclic thioether, or combinations thereof. In a further aspect, the reactant may an unsubstituted olefin, a monosubstituted olefin, a polysubstituted olefin, an unsubstituted cyclic ether, a monosubstituted cyclic ether, a polysubstituted cyclic ether, an unsubstituted cyclic thioether, a monosubstituted cyclic thioether, a polysubstituted cyclic thioether, or combinations thereof. Substituent groups suitable for use within any monosubstituted reactant and/or polysubstituted reactant may include but are not limited to alkyl groups, hydrocarbyl groups, halides, organyl groups, or combinations thereof; alternatively, alkyl groups; alternatively, hydrocarbyl groups; alternatively, halides; or alternatively, organyl groups.

In a further aspect, the reactant may be any olefin suitable for producing a sulfur-containing reaction product when reacted with $H_2S$ in the presence of a solid catalyst. In yet a further aspect, the olefin may be a monoolefin comprising a $C_2$ to $C_{30}$ alpha-monoolefin, a $C_4$ to $C_{30}$ internal monoolefin, a $C_3$ to $C_{30}$ cyclic aliphatic monoolefin, a $C_8$ to $C_{30}$ aryl monoolefin or combinations thereof. The $C_2$ to $C_{30}$ alpha-monoolefin may comprise ethylene, propylene, 1-butene, isobutylene, 1-pentene and isomers thereof, 1-hexene and isomers thereof, and the like. In a particular aspect the $C_2$ to $C_{30}$ alpha-monoolefin may comprise 2-methyl-2-octene, 2-methyl-2-undecene, or a combination thereof. The $C_4$ to $C_{30}$ internal monoolefin may comprise 2-butene, 2-pentene and isomers thereof, 2-hexene and isomers thereof, 3-hexene and isomers thereof, and the like. In a particular aspect the $C_4$ to $C_{30}$ internal monoolefin may comprise 2-butene, 2-methyl-2-butene, 2,3-dimethyl-2-butene, or a combination thereof. The $C_3$ to $C_{30}$ cyclic aliphatic monoolefin may comprise cyclopropene, cyclobutene, cyclopentene, cyclohexene, cycloheptene, cyclooctene, cyclononene, cyclodecene, cycloundecene, cyclododecene, and the like. In yet a further aspect, the $C_8$ to $C_{30}$ aryl monoolefin may comprise styrene.

In a further aspect, the reactant may be any cyclic ether suitable for producing a sulfur-containing reaction product when reacted with $H_2S$ in the presence of a solid catalyst. In an aspect, the cyclic ether may be a $C_2$ to $C_{30}$ oxirane, a $C_3$ to $C_{30}$ oxetane, a $C_4$ to $C_{30}$ tetrahydrofuran, a $C_5$ to $C_{30}$ tetrahydropyran, and the like. In some aspects, the cyclic ether may be ethylene oxide (i.e., oxirane), propylene oxide, 1,1-dimethyl oxirane, 1,2,-dimethyl oxirane, trimethyl oxirane, tetramethyl oxirane, oxetane, tetrahydrofuran, tetrahydropyran, or combinations thereof.

In a further aspect, the reactant may be any cyclic thioether suitable for producing a sulfur-containing reaction product when reacted with $H_2S$ in the presence of a solid catalyst. In an aspect, the cyclic thioether may be a $C_2$ to $C_{30}$ thiirane, a $C_3$ to $C_{30}$ thietane, a $C_4$ to $C_{30}$ tetrahydrothiophene, and the like. In some aspects, the cyclic thioether may be ethylene sulfide (i.e., thiirane), propylene sulfide, 1,1-dimethyl thiirane, 1,2,-dimethyl thiirane, trimethyl thiirane, tetramethyl thiirane, thietane, tetrahydrothiophene, or a combination thereof.

In an aspect, the sulfur-containing reaction product comprises a mercaptoalcohol, a mercaptan, a dithiol or combinations thereof. In a further aspect, the mercaptoalcohol may be a branched mercaptoalcohol or a non-branched mercaptoalcohol. In a further aspect, the mercaptan may be a linear mercaptan, a cyclic mercaptan, or a combination thereof, wherein the linear mercaptan may be a branched mercaptan or a non-branched mercaptan. In a further aspect, the dithiol may be a branched dithiol or a non-branched dithiol. In yet a further aspect, the sulfur-containing reaction product may an unsubstituted mercaptoalcohol, a monosubstituted mercaptoalcohol, a polysubstituted mercaptoalcohol, an unsubstituted mercaptan, a monosubstituted mercaptan, a polysubstituted mercaptan, an unsubstituted dithiol, a monosubstituted dithiol, a polysubstituted dithiol, or combinations thereof. Substituent groups suitable for use within any monosubstituted reactant and/or polysubstituted reactant may include but are not limited to alkyl groups, hydrocarbyl groups, halides, organyl groups, or combinations thereof; alternatively, alkyl groups; alternatively, hydrocarbyl groups; alternatively, halides; or alternatively, organyl groups.

In an aspect, the sulfur-containing reaction product may be a $C_2$ to $C_{30}$ β-mercaptoethanol, a $C_2$ to $C_{30}$ γ-mercaptopropanol, a $C_2$ to $C_{30}$ δ-mercaptobutanol, a $C_2$ to $C_{30}$ ε-mercaptopentanol, or combinations thereof. In a further aspect, the mercaptoalcohol may be 2-mercapto-1-ethanol (β-mercaptoethanol, BME), 1-mercapto-2-propanol, 2-mercapto-1-propanol, 2-mercapto-2-methyl-1-propanol, 1-mercapto-2-methyl-2-propanol, 3-mercapto-2-butanol, 3-mercapto-3-methyl-2-butanol, 3-mercapto-2-methyl-2-butanol, 3-mercapto-2,3-dimethyl-2-butanol, 3-mercapto-1-propanol, 4-mercapto-1-butanol, 5-mercapto-1-pentanol or combinations thereof. In a particular aspect, the mercaptoalcohol may be 2-mercapto-1-ethanol (β-mercaptoethanol, BME).

In a further aspect, the sulfur-containing reaction product may be a $C_2$ to $C_{30}$ primary mercaptan, a $C_2$ to $C_{30}$ secondary mercaptan, a $C_2$ to $C_{30}$ tertiary mercaptan, or combinations thereof. In an aspect, the reaction product may be ethyl mercaptan, n-propyl mercaptan, isopropyl mercaptan, n-butyl mercaptan, butyl-2-mercaptan, sec-butyl mercaptan, tert-butyl mercaptan, 2-methyloctyl mercaptan, tert-nonanyl mercaptan, 2-methylundecyl mercaptan, tert-dodecanyl mercaptan, cyclopropyl mercaptan, cyclobutyl mercaptan, cyclopentyl mercaptan, cyclohexyl mercaptan, 2-methylbutyl-2-mercaptan, 3-methylbutyl-2-mercaptan, 2,3-dimethylbutyl-2-mercaptan, phenylethyl-1-mercaptan, phenylethyl-2-mercaptan, or combinations thereof.

In yet a further aspect, the sulfur-containing reaction product may be a $C_2$ to $C_{30}$ β-dithiol, a $C_2$ to $C_{30}$ γ-dithiol, a $C_2$ to $C_{30}$ δ-dithiol or combinations thereof. In an aspect, the reaction product may be ethane-1,2-dithiol, 1-methylethane-1,2-dithiol, 2-methylpropane-1,2-dithiol, butane-2,3-dithiol, 2-methylbutane-2,3-dithiol, 2,3-dimethylbutane-2,3-dithiol, propane-1,3-dithiol, butane-1,4-dithiol, or combinations thereof.

Fixed Bed Catalytic Reactor

In an aspect, the reactor can comprise any suitable fixed bed catalytic reactor. Generally, a fixed bed catalytic reactor contains a fixed bed of solid catalyst, wherein the solid catalyst does not move with respect to a fixed or immobile reference point on a reactor body. The solid catalyst can be retained in the fixed bed by any suitable methodology, such as for example by employing retaining screens.

In an aspect, the fixed bed catalytic reactor can be a continuous flow reactor, such as a plug flow reactor (PFR). Generally, a PFR, also known as a flow tube reactor, comprises a fluid flowing through the reactor as a series of infinitely thin coherent "plugs," each plug having a uniform composition, traveling in the axial direction of the flow tube reactor. In PFRs, it is assumed that as a plug flows through the reactor, the fluid is perfectly mixed in the radial direction, but not in the axial direction (forwards or backwards).

In an aspect, the reactor can be an adiabatic reactor. Generally, adiabatic reactors do not provide for heat exchange between the interior of the reactor (e.g., catalyst, catalyst bed, reactants, etc.) and the surroundings of the reactor. In an aspect, no internal and/or external cooling source is used to cool the reactor. For purposes of the disclosure herein, the term "internal cooling" excludes evaporative cooling due to (e.g., owing to) hydrogen sulfide converting from a liquid phase to a vapor phase, thereby absorbing a heat of reaction. In aspects, cooling equipment which are not used for external cooling include heat exchangers and reactor jackets. In aspects, cooling equipment which are not used for internal cooling include internal heat exchange elements (e.g., heat exchange elements that would be placed inside the reactor) that can contain a heat transfer medium (i.e., a heat transfer fluid such as water, mineral oil(s), synthetic or organic based fluid(s), or combinations thereof). Further, for purposes of the disclosure herein, the terms "internal cooling" and "external cooling" refer to cooling by heat exchange based on energy input outside of the reactor. The adiabatic reactor as used herein can be a "self-cooling" reactor via converting (e.g., evaporating) hydrogen sulfide from a liquid phase to a vapor phase. As will be appreciated by one of skill in the art, and with the help of this disclosure, the reaction of an oxirane with hydrogen sulfide to produce a hydroxymercaptan is exothermic, as will be discussed in more detail later herein.

Catalyst

The solid catalyst of the present disclosure can include any solid catalyst suitable for producing a sulfur-containing reaction product via conversion of a reactant in an excess of hydrogen sulfide ($H_2S$). In a particular aspect, the solid catalyst may be a zeolite. Zeolites are microporous solids wherein the term "microporous" generally refers to a well-defined pore size of less than about 20 Angstroms (Å). Varieties of zeolites include naturally occurring minerals and chemically synthesized materials. In addition to the well-defined pore size, they are characterized by high melting points common to naturally occurring solid minerals, high structural uniformity, large surface area, complete crystallinity and excellent reproducibility. More than 230 unique zeolite frameworks have been identified, and more than 40 naturally occurring zeolite frameworks are known. In an aspect, the zeolite suitable for use as disclosed herein may be an aluminosilicate zeolite, a silicate zeolite, an aluminophosphate zeolite, a galliumphosphate zeolite, or combinations thereof. In a specific aspect, the zeolite suitable for use as the solid catalyst may be an aluminosilicate zeolite (i.e., AS-Z).

The basic structural units of an aluminosilicate zeolite (i.e., AS-Z) are tetrahedral units comprising either a silicon atom or an aluminum atom coordinated with four oxygen atoms. The oxygen atoms are mutually shared between two tetrahedral units wherein each tetrahedral unit contributes one of the two valence charges of each oxygen atom. Since aluminum atoms are trivalent, each $AlO_4$ unit is negatively charged and the charge must be balanced by cations (e.g., metal cations). An AS-Z further comprises an open framework structure centered upon a building block called a sodalite cage, which is a truncated octahedron unit consisting of 24 $SiO_4$—$AlO_4$ units. An array of sodalite cages throughout the AS-Z are connected through 4 of the 8 faces of the octahedron in a tetrahedral arrangement. The open framework structure further comprises 12-membered rings of oxygen atoms wherein the rings define individual pores of the AS-Z array and wherein the pores open into channels of the AS-Z framework. In an aspect, the AS-Z comprises a characteristic pore size diameter and a characteristic channel diameter. In a further aspect, the catalytic activity of the AS-Z may be determined by the pore size diameter, the channel diameter, or a combination thereof. In a particular aspect, the AS-Z suitable for use herein may have a pore size diameter of from about 3 Å to about 22 Å; alternatively, from about 5 Å to about 16 Å; or alternatively, from about 7 Å to about 10 Å. In a further aspect, the AS-Z may have a channel diameter of from about 3 Å to about 22 Å; alternatively, from about 10 Å to about 15 Å; or alternatively, about 11 Å to about 12 Å. In a still further aspect, the pore size diameter, the channel diameter, or a combination thereof can accommodate a wide variety of cations (e.g., $H^+$, $Na^+$, $Ca^{2+}$) that are loosely held within the AS-Z and capable of being readily exchanged.

In an aspect, the zeolite crystal structure is that of a faujasite.

In an aspect, an AS-Z suitable for use as a solid catalyst as disclosed herein may be Type Y zeolite, a Type X zeolite, or a combination thereof. Generally, the chemical composition of Type Y zeolites and Type X zeolites may be expressed in terms of an oxide ratio (e.g., $Na_2O:Al_2O_3$: $SiO_2$). Alternatively, the composition of the zeolite may be written as chemical formula. For example, when a Type Y zeolite having a $SiO_2:Al_2O_3$ oxide ratio of 4.8 is hydrated a composition of a hydrated unit cell may be written as $Na_{56}[(AlO_2)_{56}(SiO_2)_{136}] \cdot 264H_2O$. In a further example, the composition a hydrated Type X zeolite may be written as $Na_{86}[(AlO_2)_{86}(SiO_2)_{106}] \cdot 264H_2O$. Without wishing to be bound by theory, the AS-Z comprises a molar ratio of Si to Al that may determine the acid character of the AS-Z, the catalytic activity of the AS-Z, or both. For purposes of the present disclosure, the molar ratio of Si to Al of the AS-Z is defined as a ratio of moles of Si to moles of Al within a zeolite and is distinguished from an oxide ratio of silica to alumina (i.e., $SiO_2:Al_2O_3$ oxide ratio) as disclosed herein. In an aspect, the AS-Z comprises a molar ratio of Si to Al in a range of from about 1.2 to about 3; alternatively, from about 2.1 to about 2.7; or alternatively, from about 2.1 to about 2.3.

In yet a further aspect, an AS-Z suitable for use as a solid catalyst as disclosed herein comprises metal cations. In an aspect, the metal cations comprise $Na^+$. In a further aspect, the metal cations may determine the chemical properties of the zeolite. In a further aspect, the $Na^+$ cations may be held loosely within the AS-Z and may be capable of being readily exchanged. For example, when the AS-Z is immersed within an aqueous liquid, hydronium ions ($H_3O^+$) of the liquid can exchange with $Na^+$ cations of the AS-Z. Without wishing to be limited by theory, a concentration of $H_{30}^+$ in the aqueous liquid may decrease as $H_{30}^+$ is replaced by $Na^+$ cations of the AS-Z, wherein the decrease in $H_{30}^+$ causes an increase in the pH value of the aqueous liquid. In an aspect, the AS-Z may increase a concentration of sodium hydroxide (NaOH) ions in the aqueous liquid upon being immersed in the aqueous liquid.

In an aspect, a solid catalyst of the present disclosure may be any solid catalyst (e.g., zeolite, AS-Z) comprising acidic active groups suitable for producing a sulfur-containing reaction product via conversion of a reactant in an excess of hydrogen sulfide. In a further aspect, the acidic active groups of the zeolite (e.g., AS-Z) may comprise Brønsted acid sites, Lewis acid sites, or a combination thereof. For purposes of the present disclosure, the Brønsted acid sites may comprise acidic protons. In a further aspect, the Brønsted acid sites may be hydrogen ions or hydronium ions bonded to oxygen atoms of a zeolite framework. In other words, the Brønsted acid sites may be protic groups (e.g., $OH^+$) bound to silicon, aluminum, or a combination thereof, wherein the protic groups may donate acidic protons to the surroundings. In a further aspect, the Lewis acid sites may be electron deficient sites comprising one or more unoccupied orbitals capable of accepting electrons from the surroundings. The Lewis acid sites may comprise aluminum or an oxide thereof, silicon or an oxide thereof, an oxide particle, or combinations thereof. In a still further aspect, the Lewis acid sites may be neutral or, alternatively may comprise a net positive charge.

In a further aspect, a solid catalyst suitable for use as disclosed herein may be a Type Y zeolite such as LZY-54 or LZY-64 which are commercially available from Honeywell. In an aspect, the solid catalyst may be LZY-64. In yet a further aspect, the solid catalyst may be a Type X zeolite such as 13X molecular sieves which are commercially available from Sigma-Aldrich. Type Y zeolite can be distinguished from Type X zeolite by certain factors including, but not limited to, the improved hydrolytic stability and exceptional stability at elevated temperatures exhibited by Type Y as compared to Type X. Type Y and Type X zeolites also have measurably different silicon to alumina ratios, with Type Y having a higher ratio. Because of the methods (known as dealumination) required to produce Type Y zeolites, Type Y zeolites are inherently more acidic than Type X zeolites.

In an aspect, the zeolite catalyst can be either prepared using either an alumina binder or a clay binder. The catalyst can be either a pellet or a spherical shape. The size of the catalyst can be from ¹⁄₂₅ inch to ¼ inch. More preferably the catalyst is ¹⁄₂₀ inch to ⅛ inch. in diameter. The alumina bound Type Y zeolites are the catalysts used in the examples.

In a still further aspect, the solid catalyst may be an acid washed clay, an acid washed bentonite, a tetrafluoroethylene polymer resin modified with perfluorovinyl ether groups terminated with sulfonate groups, or a macroreticular sulfonated crosslinked copolymer of styrene and divinyl benzene.

Inert Diluent and Catalytic Zones

In an aspect, the fixed bed of the solid catalyst can further comprise a chemically inert solid diluent or bulking material. Non-limiting examples of chemically inert solid diluents suitable for use in the current disclosure as part of the fixed bed include fused alumina, polystyrene, copolymers of styrene and divinylbenzene (DVB), polyacrylic esters, polyethylene, polypropylene, copolymers thereof, and the like, or combinations thereof.

In some aspects, the fixed bed of the solid catalyst can comprise a single zone (e.g., single catalytic zone) comprising the solid catalyst and optionally the chemically inert solid diluent, for example the bed materials being uniformly mixed.

In other aspects, the fixed bed of the solid catalyst can comprise two or more zones (e.g., catalytic zones), wherein each zone comprises the solid catalyst and optionally the chemically inert solid diluent. When the fixed bed of the solid catalyst comprises two or more zones (e.g., catalytic zones), the solid catalyst can be distributed along the fixed bed according to a volumetric concentration gradient. For example, a volumetric concentration of the solid catalyst can increase from an entry point into a catalyst bed (e.g., reagents entry point(s)) to an exit point from the catalyst bed (e.g., reaction product exit point), e.g., a volumetric concentration of the solid catalyst can increase along a catalyst bed in the direction of the flow through a flow reactor. In some aspects, an increase in the volumetric concentration of the solid catalyst can be continuous along a length of the fixed bed or zone thereof. In other aspects, the increase in the volumetric concentration of the solid catalyst can be stepwise across a length of the fixed bed or zone thereof. As another example, a volumetric concentration of the solid catalyst can decrease from an entry point into a catalyst bed (e.g., reagents entry point(s)) to an exit point from the catalyst bed (e.g., reaction product exit point), e.g., a volumetric concentration of the solid catalyst can decrease along a catalyst bed in the direction of the flow through a flow reactor. As yet another example, a volumetric concentration of the solid catalyst can decrease along some regions or zones of the catalyst bed, increase along other regions of the catalyst bed, and stay the same along yet other regions of the catalyst bed. The amount of chemically inert solid diluent can likewise be adjusted or varied across the reactor bed geometry (e.g., along a length of the fixed bed or zone thereof) to provide a desired solid catalyst volumetric concentration profile.

In some aspects, the solid catalyst can be distributed evenly along the fixed bed, e.g., the volumetric concentration of the catalyst can stay the same along a length of the fixed bed or zone thereof, for example uniformly mixed with chemically inert solid diluent, if present.

In an aspect, the fixed bed of the solid catalyst can comprise a top zone, a middle zone, and a bottom zone, wherein the flow in the reactor can be from a top zone towards a bottom zone, and wherein the middle zone can be located between the top zone and the bottom zone. In such aspect, the top zone comprises both a solid catalyst and a chemically inert solid diluent, wherein an amount of the chemically inert solid diluent by volume is greater (e.g., greater than 50%, 55%, 60%, 65%, 70%, 75%, 80%, 85%, 90%, 95%, or 99%, based on a total volume of the top zone) than an amount of the solid catalyst by volume in the top zone; the middle zone comprises both a solid catalyst and a chemically inert solid diluent, wherein an amount of the chemically inert solid diluent by volume is about the same (e.g., about 45/55, about 50/50, about 55/45, based on volumetric ratios of chemically inert solid diluent to solid catalyst in the middle zone) as an amount of the solid catalyst by volume in the middle zone; and wherein the bottom zone comprises a solid catalyst and a lesser amount by volume (e.g., less than 50%, 45%, 40%, 35%, 30%, 25%, 20%, 15%, 10%, 5%, 1%, or 0%, based on a total volume of the bottom zone) of the chemically inert solid diluent.

In an aspect, the solid catalyst can be present in the fixed bed or any zone thereof in an amount of from about 10 vol. % to about 100 vol. %, alternatively from about 25 vol. % to about 100 vol. %, or alternatively from about 33 vol. % to about 66 vol. %, based on the total volume of the fixed bed or zone thereof.

In an aspect, the fixed bed of the solid catalyst can comprise a top zone, a middle zone, and a bottom zone; wherein the top zone includes about 66% of a chemically inert solid diluent and about 33% solid catalyst by volume; wherein the middle zone includes about 50% of the chemically inert solid diluent and about 50% solid catalyst by volume; and wherein the bottom zone includes about 100% solid catalyst by volume.

Feed Streams into Reactor

In an aspect, one or more feed streams can feed one or more reactants as described herein to the reactor. In an aspect, a feed stream can feed an olefin, a cyclic ether, a cyclic thioether, or combinations thereof (as described herein) to the reactor. In an aspect, an oxirane stream can feed an oxirane to the reactor. In an aspect, a hydrogen sulfide stream can feed hydrogen sulfide to the reactor.

In an aspect, an oxirane stream can feed an oxirane (e.g., ethylene oxide) to the reactor and a hydrogen sulfide stream can feed hydrogen sulfide to the reactor, wherein the oxirane and hydrogen sulfide react to form a hydroxymercaptan (e.g., BME). In an aspect, during steady state operation of the reactor, the hydrogen sulfide and the oxirane can be present in a mole ratio of hydrogen sulfide to the oxirane in a range of from about 5:1 to 50:1, alternatively from about 9:1 to about 20:1, alternatively from about 10:1 to about 19:1, or alternatively from about 11:1 to about 18:1. As will be appreciated by one of skill in the art, and with the help of this disclosure, hydrogen sulfide is always present in excess of the oxirane. Prior to reaching a steady state operation of the reactor, hydrogen sulfide can be introduced to the reactor prior to introducing the oxirane to the reactor, such that there is always hydrogen sulfide present in excess of the oxirane. Similarly, when the production needs to be stopped (e.g., reactor maintenance, catalyst regeneration, reactor troubleshooting, etc.), the oxirane introduction to the reactor can be stopped first, followed by stopping the hydrogen sulfide introduction to the reactor. In some aspects, a flow of hydrogen sulfide into the reactor could be maintained for a time period of from about 1 minute to about 1 hour, alternatively from about 5 minutes to about 45 minutes, or alternatively from about 15 minutes to about 30 minutes, prior to starting and/or subsequent to stopping the flow of the oxirane into the reactor. As will be appreciated by one of skill in the art, and with the help of this disclosure, the reactor is not at steady state while only hydrogen sulfide flows through the reactor, and there is no flow of the oxirane to the reactor, as both reactants are necessary to establish a steady state in the reactor. Further, as will be appreciated by one of skill in the art, and with the help of this disclosure, the oxirane is an extremely reactive compound, and as such it needs to be introduced to the reactor only when hydrogen sulfide is already present in the reactor, in order to avoid participation of the oxirane in any other reactions besides with hydrogen sulfide.

In an aspect, the oxirane stream and the hydrogen sulfide stream can each connect directly to the reactor without mixing the oxirane and hydrogen sulfide prior to introduction to the reactor. In such aspect, the oxirane stream and the hydrogen sulfide stream are separate streams introduced independent from each other to the reactor. In an aspect, the oxirane stream and the hydrogen sulfide stream can each be controlled independently from each other.

In an aspect, a thermocouple can be placed in the oxirane stream where it enters the reactor, wherein the thermocouple can be linked to a controller configured to stop a flow of the oxirane stream upon detecting a temperature in the oxirane stream which is above a threshold temperature. In some aspects, the threshold temperature can be equal to or greater than about 30° C., alternatively equal to or greater than about 35° C., or alternatively equal to or greater than about 40° C. The threshold temperature is indicative of a reaction occurring. Since the reactor is adiabatic, temperature control in the reactor can occur by monitoring the amount of material available to react. As will be appreciated by one of skill in the art, and with the help of this disclosure, the reaction between the oxirane (e.g., ethylene oxide) and hydrogen sulfide to produce a hydroxymercaptan (e.g., BME), is exothermic. Without wishing to be limited by theory, the reaction between the oxirane and hydrogen sulfide to produce the hydroxymercaptan is self-sustained (e.g., the reaction can progress by itself in the absence of an initiator and/or catalyst) at temperatures above 30-35° C., so if such temperatures are detected prior to reaching the catalyst bed, it indicates the reaction is occurring (for example, in an undesirable location outside the catalyst bed, or for example in a feed line to the reactor, a reactor head space, etc.).

In some aspects, the reaction between the oxirane and hydrogen sulfide to produce a hydroxymercaptan can be restricted to the fixed bed comprising the zeolite catalyst. Without wishing to be limited by theory, the zeolite catalyst enables the formation of the hydroxymercaptan with only a very small amount of a thiodiglycol (TDG) produced, and without any detectable formation of heavies such as an ethanedithiol (EDT). However, if the oxirane and hydrogen sulfide were to react in the absence of the zeolite catalyst, such as upstream of the fixed bed, undesirable heavies such as an EDT can form. As such, if a temperature above 30-35° C. indicative of reaction is detected in the reactor upstream of the fixed bed (and proximate to one or more thermocouples monitoring said temperature), then the flow of the oxirane can be stopped in order to stop the reaction outside the fixed bed, where reaction in the absence of the zeolite catalyst could lead to formation of undesirable heavies such as an EDT.

In some aspects, the oxirane stream and the hydrogen sulfide stream can each be connected to a mixing stream or a header such that the oxirane and hydrogen sulfide are mixed prior to introduction to the reactor. In such aspects, a thermocouple can be placed in an end of the mixing stream or within the header which is connected to the reactor, wherein the thermocouple can be linked to a controller configured to stop a flow of the oxirane stream upon detecting a temperature in the mixing stream which is above the threshold temperature, where threshold temperature is indicative of reaction (e.g., a reaction producing an undesired EDT), as previously described herein.

In an aspect, the hydrogen sulfide ($H_2S$) can be fed to the reactor in a downflow orientation. As the $H_2S$ travels along the length of the fixed bed of the reactor, a temperature of the fixed bed can increase along the length of the reactor in the direction of the flow, and some of the $H_2S$ will convert from a liquid phase to a gas phase (e.g., a portion of the liquid $H_2S$ will vaporize), thereby absorbing a portion of the reaction heat and controlling the temperature inside the reactor. The reactor is designed as an adiabatic packed bed reactor with no internals for transferring the heat of reaction. The diameter is sufficiently large so that the heat transferred through the outside walls is small relative to the heat released by the reaction. The oxirane and $H_2S$ feeds enter the top of the reactor as liquid. Once entering the catalyst bed the heat of reaction converts at least a portion of the liquid $H_2S$ into a gas. Then the reactor is operated as a typical trickle-bed reactor with liquid and gas flow concurrently flowing downward through the packed bed while reaction takes place. Co-current downward flow provides the best hydrodynamic flow patterns with the catalyst particle sizes of interest and avoids the need of internals to keep the catalyst bed intact inside of the reactor.

Reaction Conditions

The disclosed aspects include a temperature range and pressure range for the conversion of a reactant to a sulfur-containing reaction product, by reacting the reactant with hydrogen sulfide in the presence of a solid catalyst (e.g., zeolite, AS-Z), under conditions as described herein. In an aspect, hydrogen sulfide and the reactant can react in a liquid phase, wherein the liquid phase can contact the solid catalyst. As will be appreciated by one of skill in the art, and with the help of this disclosure, the temperature and pressure employed in the disclosed process are adequate to allow for the reactants to be in a liquid phase.

According to the disclosed aspects, a reactant and hydrogen sulfide may be reacted at a temperature in a range of from about 30° C. to about 220° C. in the presence of a solid catalyst (e.g., zeolite, AS-Z), to yield a sulfur-containing reaction product. In a particular aspect, an oxirane (e.g., ethylene oxide) and hydrogen sulfide can be reacted in liquid phase at a temperature in the approximate range of from about 30° C. to about 80° C. in the presence of a solid catalyst (e.g., zeolite, AS-Z), and at a molar ratio of hydrogen sulfide to the oxirane in the range of from about 9:1 to about 20:1, to yield a hydroxymercaptan (e.g., β-mercaptoethanol, BME).

In an aspect, a process for producing a sulfur-containing reaction product can be performed at a temperature (e.g., the reactor can be characterized by a temperature) in a range of from about 30° C. to about 220° C. In a particular aspect, a process for producing a hydroxymercaptan (e.g., β-mercaptoethanol, BME), can be performed at a temperature (e.g., the reactor can be characterized by a temperature) in a range of from about 30° C. to about 80° C., alternatively from about 30° C. to about 51° C., alternatively from about 35° C. to about 75° C., or alternatively from about 40° C. to about 70° C. Generally, zeolites are characterized by thermal stability at temperatures in excess of 1000° C. and retain catalytic activity when exposed to temperatures well in a range of from about 100° C. to about 500° C. Solid catalysts outside the scope of the present disclosure include ion exchange resins which are polymers that can deactivate upon exposure to high temperatures. Often catalyst longevity (e.g., length of time that a catalyst does not significantly lose catalytic activity) of the ion exchange resin catalyst can be extended by maintaining the temperature in the reactor under 80° C., but the performance and utility of the ion exchange resin as a catalyst are limited by the inability to utilize elevated reactor temperatures.

In an aspect, the fixed bed of the reactor can have a weight average bed temperature (WABT) of from about 50° C. to about 250° C., alternatively from about 50° C. to about 80° C., alternatively from about 65.5° C. to about 69.5° C., or alternatively from about 66° C. to about 69° C. Generally, the WABT is calculated for catalyst beds that do not have a uniform catalyst distribution across the reactor (e.g., multiple catalytic zones, mixtures of catalysts and inert supports used, volumetric concentration gradient of catalyst along a catalyst fixed bed or zone thereof, etc.), wherein weight fractions of the catalysts in a particular zone are correlated with the temperature of that particular zone to contribute to the averaging of the temperatures to yield the WABT. Without wishing to be limited by theory, a temperature across the catalyst bed is expected to increase along a length of the catalyst bed, in the direction of the flow through the reactor. As will be appreciated by one of skill in the art, and with the help of this disclosure, the reaction between hydrogen sulfide ($H_2S$) and an oxirane to produce a hydroxymercaptan is exothermic, and since the reaction occurs primarily in the catalyst bed, the temperature of the catalyst bed (e.g., WABT) will be higher at an exit point than at an entry point. Further, as the temperature reaches a boiling point of $H_2S$ at the pressure inside the reactor, a portion of the $H_2S$ will convert to a gas phase and absorb some of the heat of reaction, thereby preventing a temperature inside the catalyst bed from getting too high and potentially damaging the catalyst. Without wanting to be limited by theory, it is believed that the enthalpy generated during the exothermic reaction of $H_2S$ with the oxirane is sufficient to provide the latent heat of vaporization necessary to vaporize some, most, or all of the liquid $H_2S$ after it enters the reactor. In one or more aspects disclosed herein, the heat of vaporization of $H_2S$ is about 0.11 kcal/gm (about 198 BTU/lb) or about 3.7 kcal/mole (about 6,670 BTU/lbmole).

In an aspect, a process for producing a hydroxymercaptan can be performed at a pressure (e.g., the reactor can be characterized by a pressure) in a range of from about 300 psig to about 750 psig (2068-5171 kPa), alternatively from about 350 psig to about 475 psig (2413-3275 kPa, alternatively from about 450 psig to about 650 psig (2757-4482 kPa), or alternatively from about 400 psig to about 450 psig (2757-3102 kPa). In some aspects, a process for producing the hydroxymercaptan can be performed at a pressure of about 450 psig (3102 kPa). According to the disclosed aspects, a pressure in the reactor has to be high enough such that the hydrogen sulfide is a liquid at the temperature inside the reactor or catalyst bed, and at the same time the pressure cannot be too high as to prevent hydrogen sulfide vaporization when the temperature increases.

For the purposes of this disclosure, the weight hourly space velocity (WHSV) refers to a mass of oxirane fed per hour divided by a mass of active catalyst used in a particular reactor. The units for WHSV are (mass oxirane)/(mass catalyst-h), expressed and reported as $h^{-1}$. In an aspect, a weight hourly space velocity (WHSV) of the oxirane can be in a range of from about 0.1 to about 2 $h^{-1}$, alternatively from about 0.3 to about 2 $h^{-1}$, alternatively from about 0.5 to about 2 $h^{-1}$, alternatively from about 0.5 to about 0.1.5 $h^{-1}$, or alternatively from about 0.7 to about 0.1 $h^{-1}$.

Phase Transition of $H_2S$

In an aspect, a process for producing a hydroxymercaptan can further comprise converting, in the reactor, at least a portion of the hydrogen sulfide from a liquid phase to a vapor phase to absorb a heat of reaction created in the step of reacting. The reaction of an oxirane with hydrogen sulfide to produce a hydroxymercaptan is exothermic, and since in an aspect the reactor does not employ an external cooling fluid or internal heat exchange elements or devices, converting at least a portion of the hydrogen sulfide from a liquid phase to a vapor phase allows for temperature control inside the reactor (e.g., adiabatic reactor). As previously described, the heat of reaction generated from the reaction with hydrogen sulfide and the oxirane is sufficient to provide the latent heat of vaporization necessary for the hydrogen sulfide in the reactor to transition from the liquid state into vapor. Without wishing to be limited by theory, for the reactor to operate adiabatically, or near adiabatically, the heat of reaction generated is essentially equal to the latent heat of vaporization of hydrogen sulfide. Therefore the total enthalpy in the reactor is zero or close to zero, allowing the equilibrium between the heat of reaction and heat of vaporization to essentially control the temperature within the reactor.

In an aspect, the step of reacting an oxirane with hydrogen sulfide, and the step of converting at least a portion of the hydrogen sulfide from a liquid phase to a vapor phase can occur about simultaneously.

In some aspects, a process for producing a hydroxymercaptan can further comprise recovering a vapor phase of the hydrogen sulfide from the reactor; condensing at least a portion of the vapor phase of the hydrogen sulfide to a liquid phase; and recycling at least a portion of the liquid phase of the hydrogen sulfide to the reactor (e.g., to the hydrogen sulfide stream).

Effluent Stream

In an aspect, one or more effluent streams can flow out of the reactor, wherein the one or more effluent streams can comprise a sulfur-containing reaction product. In an aspect, a reactor effluent stream can comprise a mercaptoalcohol, a mercaptan, a dithiol or combinations thereof, as described herein.

In an aspect, an effluent stream can flow out of the reactor, wherein the effluent stream can comprise a reaction product comprising a hydroxymercaptan (e.g., BME) that is produced in the reactor by a reaction of hydrogen sulfide and an oxirane (e.g., ethylene oxide) in liquid phase in presence of the solid catalyst (e.g., a zeolite catalyst). For purposes of the disclosure herein, the term "reaction product" includes but is not limited to any reaction products that are produced by the reaction between hydrogen sulfide and the oxirane, including primarily the hydroxymercaptan (e.g., BME), and any unreacted oxirane. Further, for purposes of the disclosure herein, the term "reaction product" is defined on a hydrogen sulfide-free basis, e.g., the reaction product excludes hydrogen sulfide.

In an aspect, the effluent stream can comprise the reaction product and hydrogen sulfide. In such aspect, the effluent stream can be subjected to a separation step to separate the hydrogen sulfide from the reaction product. For example, the effluent stream can be introduced to a high pressure stripping column wherein the hydrogen sulfide is vaporized and recovered as hydrogen sulfide vapor phase (overhead stream), which can be subsequently condensed and recycled back to the reactor. The reaction product can be recovered as a bottoms stream from the high pressure stripping column.

In an aspect, $H_2S$ is the only reaction component that is recycled back to the reactor. In such aspect, the product stream is not subjected to any separation steps other than removal of $H_2S$, for example by a stripping column.

Figure 2:
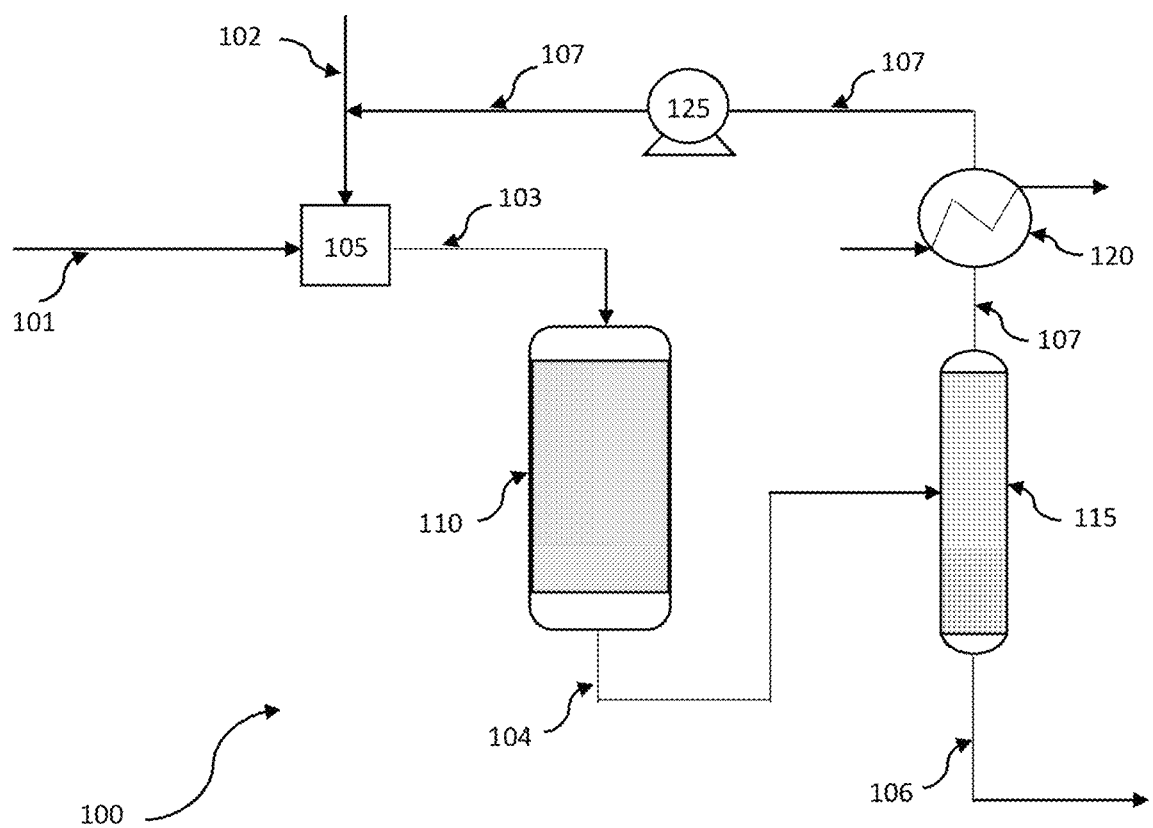
FIG. 2 is a basic block flow diagram of the process for making beta-mercaptoethanol.

FIG. 2 shows a simple block diagram depicting System 100, which depicts a basic hydroxymercaptan production process. At a minimum, a hydroxymercaptan production process as depicted by System 100 will comprise feed stream 101 comprising liquid oxirane; feed stream 102 comprising liquid $H_2S$; feed mixer 105, where the oxirane feed and $H_2S$ feed are combined; combined oxirane and $H_2S$ feed stream 103; reactor 110, where the oxirane and $H_2S$ react to form hydroxymercaptan; reactor effluent stream 104 comprising unreacted $H_2S$ and hydroxymercaptan; $H_2S$ stripper 115, where $H_2S$ is separated from hydroxymercaptan product; product stream 106 comprising $H_2S$-free hydroxymercaptan; heat exchanger 120, which cools the $H_2S$ stream leaving $H_2S$ stripper 115; recycle stream 107 comprising $H_2S$; and pump 125, which moves $H_2S$ recycle stream 107 so that it can be combined with stream 102.

As one of ordinary skill in the art would recognize, there may be additional equipment in the process including, but not limited to, pumps and heat exchangers (in addition to heat exchanger 120 and pump 120, as shown in FIG. 2), compressors, valves, and the like. Reactor 110 can be a plug flow reactor. $H_2S$ may be separated from hydroxymercaptan product using one or more $H_2S$ stripper columns in series. Noticeably absent from System 100 is any recycle of oxirane feed, hydroxymercaptan product, or further purification of hydroxymercaptan product. Reactor 110 can achieve greater than 85 wt. % conversion of oxirane in a single pass, with no recycle of oxirane. The hydroxymercaptan product leaving $H_2S$ stripper 115 (or the last $H_2S$ stripper, if the process comprises more than one in series) comprises 99 wt. % or greater hydroxymercaptan with no further downstream separation.

In an aspect, the reaction product in the effluent can consist essentially of a hydroxymercaptan and a thiodiglycol (TDG), (e.g., the reaction product can comprise less than about 1 wt. %, less than about 0.1 wt. %, less than about 0.01 wt. %, or less than about 0.001 wt. % of the unreacted oxirane, based on a total weight of the reaction product). In an aspect, an effluent of the reactor (e.g., effluent stream) can comprise the reaction product, wherein the reaction product in the effluent further comprises equal to or greater than about 80 wt. %, alternatively equal to or greater than about 85 wt. %, alternatively equal to or greater than about 90 wt. %, alternatively equal to or greater than about 95 wt. %, alternatively equal to or greater than about 99 wt. %, alternatively equal to or greater than about 99.2 wt. %, alternatively equal to or greater than about 99.4 wt. %, alternatively equal to or greater than about 99.6 wt. %, or alternatively equal to or greater than about 99.9 wt. % of a hydroxymercaptan (with any remainder comprising a TDG and/or unreacted oxirane). According to the aspects of this disclosure, it is possible to produce a reaction product having upwards of 99 wt. % purity of a hydroxymercaptan. In a further embodiment, it is possible to produce a reaction product comprising equal to or greater than 99 wt. % purity of a hydroxymercaptan with no additional separation steps other than removal of $H_2S$. As one of ordinary skill in the art would recognize, the ability to produce a high-purity hydroxymercaptan product without having to employ additional separation steps is preferable because it reduces the capital and operating costs of the process.

In an aspect, an effluent of the reactor (e.g., effluent stream) can comprise the reaction product, wherein the reaction product in the effluent further comprises less than about 20 wt. %, alternatively less than about 13 wt. %, alternatively less than about 6 wt. %, alternatively less than about 1 wt. %, alternatively less than about 0.5 wt. %, alternatively less than about 0.25 wt. %, alternatively less than about 0.1 wt. %, alternatively less than about 0.05 wt. %, or alternatively less than about 0.01 wt. % of a thiodiglycol (TDG) and/or unreacted oxirane. The TDG can form by exothermic reaction of a hydroxymercaptan with the oxirane. As will be appreciated by one of skill in the art, and with the help of this disclosure, TDG is generally present as an undesirable product (e.g., impurity) in reaction products from hydroxymercaptan production processes. Without wishing to be limited by theory, an aluminosilicate zeolite (AS-Z) as disclosed herein selectively catalyzes the formation of the hydroxymercaptan from the oxirane and hydrogen sulfide, and as such only a very low amount of undesirable products such as TDG are formed, or no amount of undesirable products such as TDG are formed. Without wishing to be limited by theory, the selectivity in formation of the hydroxymercaptan from the oxirane may be directed by a pore size diameter of the AS-Z, a channel diameter of the AS-Z, or a combination thereof.

In some aspects, the reaction product is essentially free of any thiodiglycol (TDG), e.g., the reaction product comprises no TDG. In an aspect, the reaction product consists of, or consists essentially of, a hydroxymercaptan (e.g., BME). In an aspect, no TDG can be detected (e.g., by gas chromatography) in the reaction product. In an aspect, the amount of TDG in the reaction product is 0 wt. % or 0 mol %.

In some aspects, the reaction product is essentially free of unreacted oxirane, e.g., the reaction product comprises no unreacted oxirane (e.g., ethylene oxide). In an aspect, the amount of unreacted oxirane in the reaction product is 0 wt. % or 0 mol %.

In an aspect, no detectable amount of ethanedithiol (EDT) is present in the reaction product when analyzing a sample of an effluent of the reactor via gas chromatography to two decimal places for weight percent or to three decimal places for mole percent. Conventional processes for the production of hydroxymercaptans from the reaction of an oxirane with hydrogen sulfide generally lead to the production of one or more EDTs, which is another type of undesirable product (e.g., impurity) in the reaction products, in addition to thiodiglycol (TDG).

In some aspects, the reaction product is essentially free of ethanedithiol (EDT), e.g., the reaction product comprises no EDT. In an aspect, the amount of EDT in the reaction product is 0.00 wt. % or 0.000 mol %.

Measurements can be taken with any gas chromatography technique known by those skilled in the art with the aid of this disclosure. Examples of suitable gas chromatography (GC) techniques include those which utilize a capillary column having a nonpolar stationary phase (e.g., 100% dimethylpolysiloxane). Using a capillary column as described allows for separation by component volatility (i.e., boiling point) only. Non-limiting examples of capillary columns are VF-1ms and CP-Sil 5 CB. The detector used in the GC technique may be a TCD detector or FID detector. A TCD detector can detect water and $H_2S$ in a single analysis, while FID can detect the reaction products, for example, in high purity.

Selectivity

For purposes of the disclosure herein, a selectivity to hydroxymercaptan (e.g., BME) can be calculated by dividing an amount of an oxirane (e.g., ethylene oxide) that was converted to hydroxymercaptan in a given time period in a flow reactor by the total amount of the oxirane that was converted into any reaction product, including a hydroxymercaptan, over the exact same time period in the same flow reactor. In an aspect, a process for producing the hydroxymercaptan can be characterized by a selectivity to the hydroxymercaptan (e.g., BME) of greater than about 93 wt. %, alternatively greater than about 95 wt. %, alternatively greater than about 97 wt. %, alternatively greater than about 99 wt. %, alternatively greater than about 99.5 wt. %, or alternatively greater than about 99.9 wt. %, based on a total weight of the oxirane (e.g., ethylene oxide) that was converted to the hydroxymercaptan divided by a total weight of the oxirane that was converted into the reaction product. In an aspect, an aluminosilicate zeolite (AS-Z), catalyst having acidic active groups can allow a conversion of the oxirane (e.g., ethylene oxide) with a selectivity to the hydroxymercaptan (e.g., BME) of greater than about 93 wt. %, alternatively greater than about 95 wt. %, alternatively greater than about 97 wt. %, or alternatively greater than about 99 wt. %, based on a total weight of the oxirane that was converted to hydroxymercaptan divided by a total weight of the oxirane that was converted into the reaction product. In an embodiment, the conversion of oxirane with a selectivity to the hydroxymercaptan is greater than 99.9%. In another embodiment, the conversion of oxirane with a selectivity to the hydroxymercaptan is effectively 100%. Without wishing to be limited by theory, an AS-Z, having acidic active groups could selectively enable the formation of the hydroxymercaptan, while selectively inhibiting the formation of undesirable products such as an ethanedithiol (EDT) and a thiodiglycol (TDG). Without wishing to be limited by theory, the selectivity in formation of the hydroxymercaptan may be directed by a pore size diameter of the AS-Z, a channel diameter of the AS-Z, or a combination thereof.

For purposes of the disclosure herein, a conversion of an oxirane to reaction products can be calculated by dividing an amount of the oxirane that was converted to reaction product in a given time period in a flow reactor by the total amount of the oxirane that was introduced to the same flow reactor, over the exact same time period. In an aspect, the step of reacting the oxirane (e.g., ethylene oxide) with hydrogen sulfide to produce a hydroxymercaptan (e.g., BME) can include a conversion of the oxirane to the reaction product that is greater than about 85 wt. %, alternatively greater than about 95 wt. %, alternatively greater than about 97 wt. %, alternatively greater than about 99 wt. %, alternatively greater than about 99.5 wt. %, or alternatively greater than about 99.9 wt. %, based on the weight of the oxirane that was converted to reaction product divided by the weight of the oxirane fed to the reactor.

Selectivity and Conversion of the Process

In a further aspect, a process for producing a hydroxymercaptan (e.g., BME) can comprise reacting, in an adiabatic continuous flow reactor having a fixed bed containing a solid catalyst comprising a zeolite, hydrogen sulfide and an oxirane (e.g., ethylene oxide) in the presence of the solid catalyst to yield a reaction product comprising the hydroxymercaptan wherein during steady state operation of the reactor, the hydrogen sulfide and the oxirane can be present in a mole ratio in a range of from about 5:1 to 50:1, alternatively from about about 9:1 to about 20:1; wherein the process can be performed at a temperature in a range of from about 50° C. to about 80° C., and a pressure in the range of 450 psig (3102 kPa) to 750 psig (5171 kPa); wherein the zeolite comprises an aluminosilicate zeolite having acidic active groups comprising Brønsted acid sites and Lewis acid sites; and wherein a selectivity to the hydroxymercaptan can be greater than about 93 wt. %, based on a total weight of the oxirane that was converted the hydroxymercaptan divided by a total weight of the oxirane that was converted into the reaction product.

In a further aspect, a process for producing a hydroxymercaptan (e.g., BME) can comprise reacting, in an adiabatic continuous flow reactor having a fixed bed containing a solid catalyst comprising a zeolite, hydrogen sulfide and an oxirane (e.g., ethylene oxide) in the presence of the solid catalyst to yield a reaction product comprising the hydroxymercaptan; wherein during steady state operation of the reactor, the hydrogen sulfide and the oxirane can be present in a mole ratio in a range of from about 5:1 to 50:1, alternatively from about 9:1 to about 20:1; wherein the process can be performed at a temperature in a range of from about 50° C. to about 80° C., at a WHSV of the oxirane in a range of from about 0.2 to about 2 $h^1$, and at a pressure in the range of 450 psig (3102 kPa) to 750 psig (5171 kPa); wherein the zeolite comprises LZY-54, LZY-64, or a combination thereof having acidic active groups comprising Brønsted acid sites and Lewis acid sites; and wherein a selectivity to the hydroxymercaptan can be greater than about 97 wt. %, based on a total weight of the oxirane that was converted to the hydroxymercaptan divided by a total weight of the oxirane that was converted into the reaction product.

In a further aspect, a process for producing a hydroxymercaptan (e.g., BME) can comprise reacting, in an adiabatic continuous flow reactor having a fixed bed containing a solid catalyst comprising a zeolite, hydrogen sulfide and an oxirane (e.g., ethylene oxide) in the presence of the solid catalyst to yield a reaction product comprising the hydroxymercaptan; wherein during steady state operation of the reactor, the hydrogen sulfide and the oxirane can be present in a mole ratio in a range of from about 5:1 to 50:1, alternatively from about 9:1 to about 20:1; wherein the process can be performed at a temperature in a range of from about 50° C. to about 80° C., at a WHSV of the oxirane in a range of from about 0.2 to about 2 h$^1$, and at a pressure in the range of 450 psig (3102 kPa) to 750 psig (5171 kPa); wherein the zeolite comprises LZY-64 having acidic active groups comprising Brønsted acid sites and Lewis acid sites; and wherein a selectivity to the hydroxymercaptan can be greater than about 99.0 wt. %, or alternatively, greater than 99.9 wt. %, based on a total weight of the oxirane that was converted to the hydroxymercaptan divided by a total weight of the oxirane that was converted into the reaction product.

Selectivity and Conversion of the Reactor System

In an aspect, a reactor system for producing a hydroxymercaptan (e.g., BME) can comprise an adiabatic continuous flow reactor; an oxirane stream feeding an oxirane (e.g., ethylene oxide) to the reactor; a hydrogen sulfide stream feeding hydrogen sulfide to the reactor; a fixed bed containing a solid catalyst placed in the reactor, wherein the solid catalyst comprises a zeolite with acidic active groups comprising Brønsted acid sites and Lewis acid sites; and an effluent stream flowing from the reactor, wherein the effluent stream comprises a reaction product comprising the hydroxymercaptan produced in the reactor by a reaction of hydrogen sulfide and the oxirane in the presence of the solid catalyst; wherein the hydrogen sulfide and the oxirane are present in the reactor during steady state operation in a mole ratio ranging from about 5:1 to about 50:1, alternatively from 9:1 to about 20:1; wherein the reactor operates at a temperature in a range of from about 30° C. to about 80° C. and a pressure in the range of 450 psig (3102 kPa) to 750 psig (5171 kPa); wherein a conversion of the oxirane to the reaction product comprising the hydroxymercaptan can be greater than about 85 wt. %, based on the weight of the oxirane that was converted to reaction product divided by the weight of the oxirane fed to the reactor; and wherein a selectivity to the hydroxymercaptan can be greater than about 93 wt. %, based on a total weight of the oxirane that was converted to the hydroxymercaptan divided by a total weight of the oxirane that was converted into the reaction product, and the reaction product in the effluent further comprises less than about 6 wt. % thiodiglycol on a hydrogen sulfide-free basis.

In an aspect, a reactor system for producing a hydroxymercaptan (e.g., BME) can comprise an adiabatic continuous flow reactor; an oxirane stream feeding an oxirane (e.g., ethylene oxide) to the reactor; a hydrogen sulfide stream feeding hydrogen sulfide to the reactor; a fixed bed containing a solid catalyst placed in the reactor, wherein the solid catalyst comprises LZY-54, LZY-64, or a combination thereof having acidic active groups comprising Brønsted acid sites and Lewis acid sites; and an effluent stream flowing from the reactor, wherein the effluent stream comprises a reaction product comprising the hydroxymercaptan produced in the reactor by a reaction of hydrogen sulfide and the oxirane in the presence of the solid catalyst; wherein the hydrogen sulfide and the oxirane are present in the reactor during steady state operation in a mole ratio ranging from about 5:1 to 50:1; alternatively from about 9:1 to about 20:1; wherein the reactor operates at a temperature in a range of from about 50° C. to about 80° C., at a WHSV of the oxirane in a range of from about 0.2 to about 2 h$^1$, and at a pressure in the range of 450 psig (3102 kPa) to 750 psig (5171 kPa); wherein a conversion of the oxirane to the reaction product comprising the hydroxymercaptan can be greater than about 95 wt. %, based on the weight of the oxirane that was converted to reaction product divided by the weight of the oxirane fed to the reactor; and wherein a selectivity to the hydroxymercaptan can be greater than about 97.0 wt. %, based on a total weight of the oxirane that was converted to the hydroxymercaptan divided by a total weight of the oxirane that was converted into the reaction product, and the reaction product in the effluent further comprises less than about 3 wt. % thiodiglycol on a hydrogen sulfide-free basis.

In an aspect, a reactor system for producing a hydroxymercaptan (e.g., BME) can comprise an adiabatic continuous flow reactor; an oxirane stream feeding an oxirane (e.g., ethylene oxide) to the reactor; a hydrogen sulfide stream feeding hydrogen sulfide to the reactor; a fixed bed containing a solid catalyst placed in the reactor, wherein the solid catalyst comprises LZY-64 having acidic active groups comprising Brønsted acid sites and Lewis acid sites; and an effluent stream flowing from the reactor, wherein the effluent stream comprises a reaction product comprising the hydroxymercaptan produced in the reactor by a reaction of hydrogen sulfide and the oxirane in the presence of the solid catalyst; wherein the hydrogen sulfide and the oxirane are present in the reactor during steady state operation in a mole ratio ranging from about 5:1 to 50:1, alternatively from about 9:1 to about 20:1; wherein the reactor operates at a temperature in a range of from about 50° C. to about 80° C., at a WHSV of the oxirane in a range of from about 0.2 to about 2 h$^1$, and at a pressure in the range of 450 psig (3102 kPa) to 750 psig (5171 kPa); wherein a conversion of the oxirane to the reaction product comprising the hydroxymercaptan can be greater than about 99.0 wt. %, or alternatively, greater than 99.5 wt. %, or alternatively, greater than 99.8 wt. %, or alternatively, greater than 99.9 wt. %, based on the weight of ethylene oxide that was converted to reaction product divided by the weight of the oxirane fed to the reactor; and wherein a selectivity to the hydroxymercaptan can be greater than about 99.0 wt. %, or alternatively, greater than 99.5 wt. %, or alternatively, greater than 99.8 wt. %, or alternatively, greater than 99.9 wt. %, based on a total weight of the oxirane that was converted to the hydroxymercaptan divided by a total weight of the oxirane that was converted into the reaction product, and the reaction product in the effluent further comprises less than about 1 wt. % thiodiglycol on a hydrogen sulfide-free basis.

Advantages of Present Disclosure

In an aspect, a process for producing BME as disclosed herein can advantageously display improvements in one or more process characteristics when compared to conventional processes for the production of BME. In conventional processes for the production of BME, continuous stirred-tank reactors can be employed. In an aspect, a PFR as disclosed herein can advantageously allow for safer operation. In an aspect, a process for producing BME as disclosed herein can advantageously employ an adiabatic reactor (e.g., an adiabatic PFR), which is easier to operate due to no secondary heat exchange requirement (e.g., in the case of an adiabatic reactor, there is no need to cool the reactor by using energy input from outside the reactor). In an aspect, a process for producing BME as disclosed herein can advantageously employ an adiabatic reactor (e.g., an adiabatic PFR), which is smaller (i.e., requires a smaller footprint) than a CSTR to achieve the same conversion. In an aspect, a process for producing BME as disclosed herein can advantageously employ an adiabatic reactor (e.g., an adiabatic PFR), which has lower capital and operating costs compared to a comparable CSTR reactor.

In an aspect, a process for producing BME as disclosed herein can advantageously allow for an increased selectivity in the conversion of ethylene oxide to BME (of about 99%), when compared to other conventional processes for the production of BME (typically about 92%). In an aspect, a process for producing BME as disclosed herein can advantageously allow for near quantitative conversion of ethylene oxide to reaction products (of about 99%) when compared to conventional processes for the production of BME. In a further aspect, a process for producing BME as disclosed herein can advantageously allow for near quantitative conversion of ethylene oxide to reaction products of greater than 99.0 wt. %, wherein the process is single-pass and there is no recycle of ethylene oxide.

In a further aspect, a process for producing BME as disclosed herein can advantageously allow for near quantitative conversion of ethylene oxide to reaction products of greater than 99.8 wt. %, wherein the process is single-pass and there is no recycle of ethylene oxide.

In a further aspect, a process for producing BME as disclosed herein can advantageously allow for near quantitative conversion of ethylene oxide to reaction products of greater than 99.9 wt. %, wherein the process is single-pass and there is no recycle of ethylene oxide.

In an aspect, a process for producing BME as disclosed herein can advantageously employ a solid catalyst (as opposed to a liquid catalyst or liquid initiator used in conventional processes for the production of BME), and as such the catalyst remains in the reactor and is not removed with the products, as is the case with liquid catalysts and initiators, which would further require an additional separation step to recover the products from the liquid catalysts and/or initiators. In an aspect, a process for producing BME as disclosed herein can advantageously eliminate the need for using a liquid caustic initiator for the reaction between ethylene oxide and hydrogen sulfide by using a solid catalyst.

In an aspect, a process for producing BME as disclosed herein can advantageously allow for a higher rate of production (e.g., higher BME output) owing to a higher heat exchanging capacity of the reactor.

In an aspect, a process for producing BME as disclosed herein can advantageously allow for producing a significantly lower amount of BME impurities (less than about 0.5 wt. %), such as TDG, EDT, or both, when compared to other conventional processes for the production of BME, which can produce 5-7 wt. % impurities that have to be separated and disposed of. As will be appreciated by one of skill in the art, and with the help of this disclosure, EDT has an unpleasant odor, and as such there are certain difficulties associated with EDT separation and disposal. Production of TDG is highly undesirable as it is identified in the Chemical Weapons Convention as a schedule 2 chemical that can be used to produce chemical weapons such as mustard gas. In another aspect, a process for producing BMS as disclosed herein can allow for producing a BME product stream that is at least 99 wt. % pure without any further product separation other than removal of unreacted $H_2S$. Additional advantages of the systems and/or methods for the production of a BME as disclosed herein can be apparent to one of skill in the art viewing this disclosure and include but are not limited to a smaller reactor size, a smaller reactor footprint, lower capital costs, and lower operating costs.

In a further aspect, a process for producing BME as disclosed herein can advantageously allow for an increased selectivity in the conversion of ethylene oxide to BME when utilizing an aluminosilicate Type Y zeolite (AS-Z) catalyst. Unexpectedly Type Y zeolite catalyst performs better than the Type X zeolite catalyst.

In a still further aspect, a process for producing a reaction product from a reactant and hydrogen sulfide as disclosed herein can advantageously allow for production of a wide range of reaction products. A Type Y zeolite generally displays thermal stability at temperatures in excess of 1000° C. and retains catalytic activity when exposed to temperatures well in excess of 100° C. Other commonly employed solid catalysts include ion exchange resins that can lose catalytic activity when exposed to temperatures above about 80° C. Higher process temperatures allow access to reactions and products of reactions that are inaccessible with an ion exchange resin. For example, 2-methyl-2-undecene and hydrogen sulfide may be contacted at a temperature in a range of from about 100° C. to about 150° C. in the presence of a zeolite to yield tert-dodecyl mercaptan.

Examples

The subject matter having been generally described, the following examples are given as particular aspects of the disclosure and to demonstrate the practice and advantages thereof. It is understood that the examples are given by way of illustration and are not intended to limit the specification of the claims to follow in any manner.

Catalyst Screening

Examples were performed using both propylene oxide (PO) was and ethylene oxide (EO). Propylene oxide was used as a model for the reaction in some experiments, as it is easier to handle in the lab than ethylene oxide (EO). The reaction of PO and hydrogen sulfide produces a three-carbon derivative of β-mercaptoethanol (a β-mercaptopropanol or pBME). Differences in the reaction of EO and the reaction of PO are: 1) the potential for the formation of two products from PO: 2-mercapto-1-propanol and 1-mercapto-2-propanol; and 2) lower reactivity of PO. Without wishing to be limited by theory, the major product of the PO reaction should depend upon the choice of catalyst. An acidic catalyst promotes an acid-catalyzed reaction favoring $S_N1$ addition of $H_2S$ because of the preference for the partial positive charge to reside at the more substituted carbon (FIG. 1). Conversely, a basic catalyst promotes direct $S_N2$ addition of the nucleophile to PO at the least hindered carbon. In observations associated with the following experiments 1-mercapto-2-propanol was the major product produced regardless of the type of catalyst used. Furthermore, reaction of EO from both $S_N1$ addition and $S_N2$ addition forms an identical product.

Reaction of propylene oxide to produce a 3-mercaptopropanol (pBME) was studied for various experimental conditions, such as catalyst, temperature, and reactant ratios. More specifically, the synthesis of pBME was investigated for six different catalysts: LEWATIT® K 2620 (47-53% CAS 69011-20-7) and AMBERLYST® 15 (CAS 39389-20-3), which are solid-supported acid catalysts; LEWATIT® MP-62 (CAS 9062-74-2), a solid-supported base catalyst; 13X molecular sieves (also known as a Type X zeolite; CAS 63231-69-6), and LZY-54 (1/16; CAS 1318-02-1 and 999999-99-4) and LZY-64 (1/8" extrudate, CAS 1318-02-1), which are Type-Y zeolite catalysts.

The pBME synthesis reaction from propylene oxide and $H_2S$ is highly exothermic in a manner very similar to the BME synthesis reaction from ethylene oxide shown below:

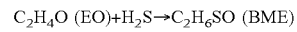

$\Delta H_{rxn}$=−75,575 BTU/lbmole

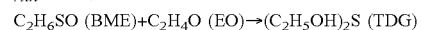

$\Delta H_{rxn}$=−75,870 BTU/lbmole

The β-mercaptopropanol (pBME) was produced in a fixed bed catalytic flow reactor operating in downflow. The reactor was a 1 inch inner diameter stainless steel jacketed reactor. Temperatures were controlled using a 50/50 glycol/water mixture flowing in an upflow configuration through the jacket. The glycol/water mixture temperature was controlled using an external Lauda RK20 constant temperature bath (of approximately 5 gallons).

During adiabatic experiments with the catalysts, there was no temperature control. The jacket temperature was raised sufficiently to initiate reaction, and then the flow of heat transfer fluid to the external jacket was stopped.

The PO and hydrogen sulfide ($H_2S$) were fed independently, and each flowrate was controlled using a Brooks mass flow controller. The two feeds were combined prior to entering the reactor and mixed in a static mixer. Static mixing was achieved by passing the feed through 2 inches of glass beads. There was a thermocouple in the reactor inlet (about 5 inches above the catalyst bed) just downstream of the static mixer. The temperature measured by this thermocouple stayed at ambient temperature throughout all of the experiments. As a standard practice, before initial introduction of PO, $H_2S$ was flowed over the reactor bed for 20 minutes.

Reaction progress was monitored by online gas chromatography and a sample port was used to take liquid samples for further analysis. Product analysis was conducted using a HP-6890 gas chromatograph (GC) equipped with a thermal conductivity detector. This method allows for quantification of crude BME, water, and $H_2S$ all in one analysis. On-line product samples were routed directly to the GC from the reactor effluent. The GC was equipped with a 30 m×0.32 mm 4.0 m film CP-Sil CB column. The initial temperature was 35° C. with a 5 min hold time and was ramped to a final temperature of 260° C. at a rate of 10° C./min with a 10 min hold time. The carrier gas was helium at a flow rate of 1.0 mL/min.—The following general experimental procedure was used for all examples, unless otherwise indicated. Propylene oxide (PO), 13X molecular sieves, and AMBERLYST® 15 were obtained from Sigma-Aldrich. Hydrogen sulfide was provided by AirGas via cylinders. LEWATIT® MP-62 was purchased manufactured by Fluka (purchased from Sigma-Aldrich). The other catalysts were obtained from their vendors; LEWATIT® K 2620 (Lanxess Corp.) and LZY-54 and LZY-64 (UOP/Honeywell). The LZ-Y54 chosen for the disclosed study was alumina bound, however a clay bound version could be substituted. The catalysts were dried in an oven at 100° C. for a minimum of 12 hours and then loaded in the reactor using a graded bed approach. ALUNDUM® (16 grit aluminum oxide) was used as the inert solid. The reactor was set up for down flow and the top third of the bed was between 30%-33% by volume active catalyst and 67%-70% by volume inert solid, the mid-section of the bed was 1:1 active catalyst to inert solid by volume, and the bottom third of the bed was 100% active catalyst, depending on the specific catalyst that was evaluated. Each of the three sections of the reactor bed comprised 19 mL of catalyst or inert solids and a 19 mL section of glass beads was located in front and behind the reactor bed. Each solid catalyst was loaded into the reactor in a similar mixed bed pattern.

LEWATIT® K 2620 is a strongly acidic, macroporous, polymer-based catalyst in spherical bead form, with sulfonic acid groups. This catalyst resulted in unacceptably low conversion at either 40° C. and 50° C. while operating at a pressure of 450 psig, a $H_2S$/PO ratio of 5:1, and a PO weight hourly space velocity (WHSV) of 0.5 $h^{-1}$. When the temperature was raised to 60° C. the reactor became plugged with an unknown solid substance believed to be oligomers of propylene oxide. This example showed that a strongly acid solid catalyst macroporous catalyst led to unacceptably high heavies formation, which led to reactor plugging at the process conditions necessary for complete oxirane conversion.

AMBERLYST® 15 is a strongly acidic, macroporous solid acid catalyst, with sulfonic acid functionality. Using this catalyst while operating at 50° C., $H_2S$/PO ratio of 5:1, and PO WHSV of 0.5 $h^{-1}$ initially gave approximately 98% conversion with approximately 90% being the pBME products; however, more than 8% heavies was also observed. Before a second sample could be taken the reactor began plugging. This example showed that, although the catalyst performed better than the LEWATIT® K 2620 solid acid catalyst in this application, there still was unacceptable reactor plugging at the process conditions necessary for complete oxirane conversion.

LEWATIT® MP 62, which is a weakly basic, macroporous anion exchange resin with tertiary amine groups, gave improved results under similar conditions. At a startup temperature of 40° C. conversion was 36% and increased to 96-98% at 50° C. with very little heavies formation wherein heavies can comprise diglycolsulfide (i.e., thiodiglycol) and dithiol side products. At 60° C. conversions exceeding 99% were obtained with less than 0.5% heavies. However, trace amounts of amines were evident in the product. This trace amine is not acceptable because of product quality concerns. This example showed that a solid base catalyst gave acceptable conversion and operability results; however, there was the adverse issue of trace amine in the product.

The 13X molecular sieves (Type X zeolite), operating at $H_2S$/PO ratio of 5:1 and PO WHSV of 0.5 $h^{-1}$, initially gave a conversion of greater than 80% at 50° C. with only approximately 0.7% heavies wherein the heavies were limited to diglycolsulfide side products (i.e., a thiodiglycol labeled pBME-S in Table 1). A subsequent sample taken approximately 90 minutes later, displayed a conversion of approximately 85% but heavies had increased to greater than 3%. At a temperature of 60° C., conversion reached 97% with approximately 2% heavies. A second sample taken 30 min later displayed a conversion closer to 95% with essentially the same heavies content. At 70° C., 98% conversion was initially observed with very little heavies formed, but a second sample showed a decrease in conversion and additional heavies present. At 80° C., the conversion was initially 97.5% with little heavies formed, but heavies then increased to more than 8%. The next series of experiments began at 70° C. and increased the PO flow to maintain a WHSV of 0.75 $h^{-1}$. Initial conversion was 93% with the same trend of increasing heavies production as the reaction continued. Increasing the $H_2S$/PO ratio to 10:1 did not reduce the heavies production at 70° C. or at 80° C. The next series of experiments were conducted on a fresh charge of molecular sieves. Operating at 70° C., $H_2S$/PO mole ratio of 10:1, and PO WHSV of 0.50 $h^{-1}$ gave a conversion similar to what had been previously observed at other conditions. The results summarized in Table 1 are averages of the individual experiments. This example shows that whereas the 13X molecular sieves (Type X zeolite) does indeed catalyze the synthesis reaction of pBME from oxirane, no conditions were found that resulted in complete oxirane conversion. Furthermore, reactor operability was compromised with increased time on-stream because of reactor plugging due to heavies formation.

TABLE 1

Summary of 13X Molecular Sieves (Type X Zeolite) Conditions and Results

| | | Temp (° C.) | | | |
|---|---|---|---|---|---|
| | | 50 | 60 | 70 | 80 |
| 0.5 WHSV | PO | 14.77 | 2.71 | 8.66 | 7.03 |
| 5:1 H2S ratio | pBME | 82.01 | 95.52 | 88.81 | 86.85 |
| | pBME-S | 2.12 | 2.51 | 1.91 | 5.83 |
| | Conversion | 84.1 | 95.0 | 90.7 | 92.7 |
| | Selectivity | 97.5 | 97.4 | 97.9 | 93.7 |
| 0.5 WHSV | PO | | | 11.57 | 11.88 |
| 10:1 H2S ratio | pBME | | | 84.82 | 83.94 |
| | pBME-S | | | 3.03 | 3.86 |
| | Conversion | | | 87.6 | 87.8 |
| | Selectivity | | | 96.6 | 95.6 |
| 0.75 WHSV | PO | | | 6.90 | |
| 5:1 H2S ratio | pBME | | | 90.62 | |
| | pBME-S | | | 2.37 | |
| | Conversion | | | 93.0 | |
| | Selectivity | | | 97.5 | |
| 0.75 WHSV | PO | | | | 5.52 |
| 10:1 H2S ratio | pBME | | | | 90.10 |
| | pBME-S | | | | 4.15 |
| | Conversion | | | | 94.3 |
| | Selectivity | | | | 95.6 |

Figure 3:
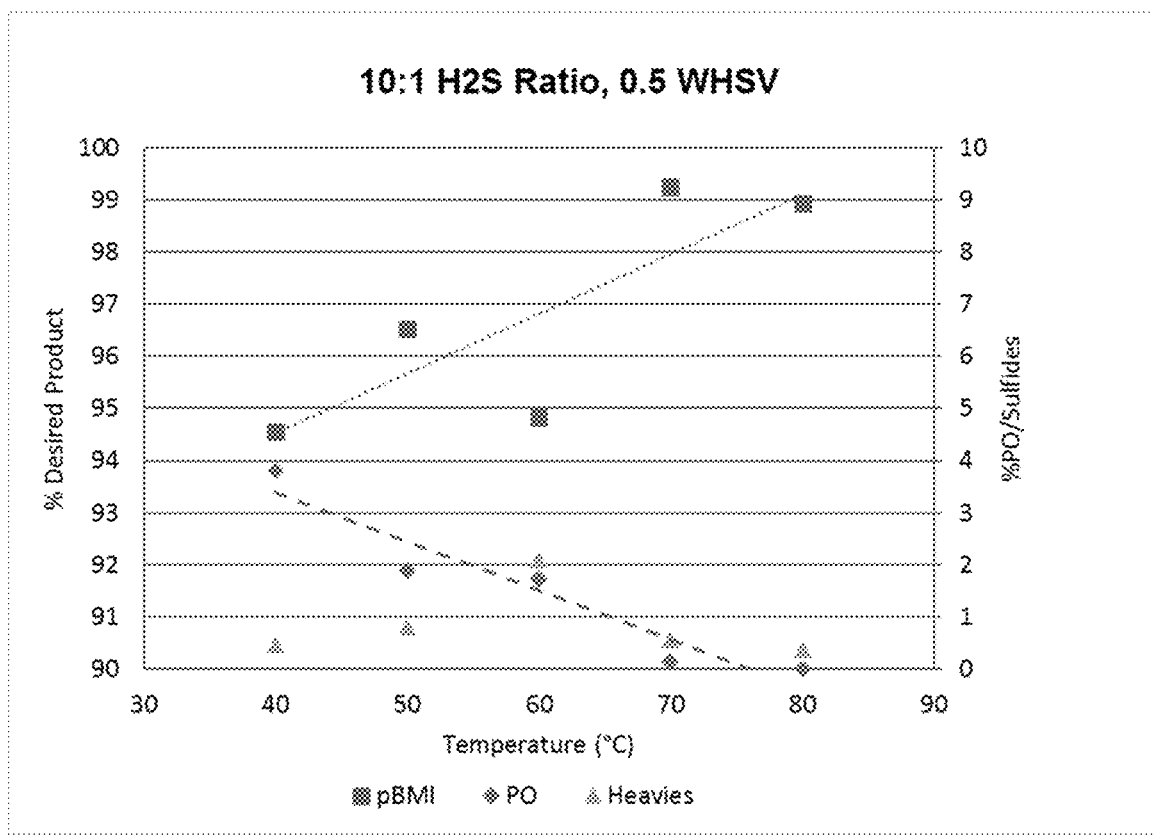
FIG. 3 is a chart of performance of LZY-54 zeolite.
Figure 4:
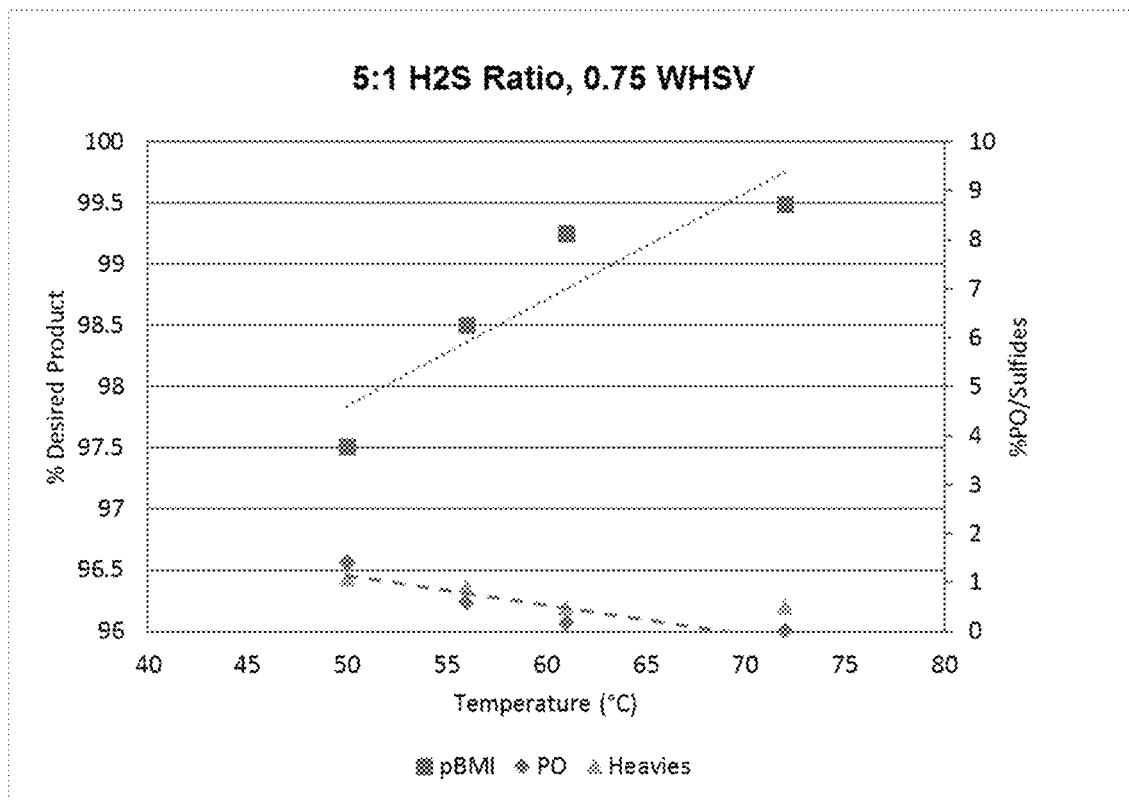
FIG. 4 is a chart of performance of LZY-54 zeolite.

LZY-54 catalyst was studied in the next experiments which were initially conducted at a H$_2$S/PO mole ratio of 10:1 and PO WHSV of 0.50 h$^{-1}$. At 60° C., conversion was initially 96% on the first day of testing with less than 0.5% heavies. On day 2, heavies increased in subsequent sampling, similar to what was observed with the 13X molecular sieves. Dropping to 50° C. kept the heavies to approximately 1% while maintaining similar conversion. At temperatures below 50° C., heavies production was observed to be similar with a slight drop in conversion. Further experiments with the LZY-54 studied a variety of conditions looking principally at three variables: temperature, WHSV, and H$_2$S/PO ratio. The results summarized in Table 2 are averages of the individual experiments. Overall, the results indicate that production of pBME at greater than about 98% purity can be achieved using LZY-54 within a very large process window. FIG. 3 and FIG. 4 display two of the most favorable sets of conditions used in conjunction with the LZY-54 catalyst. At an H$_2$S/PO mole ratio of 10:1, a PO WHSV of 0.50 h$^1$ and temperatures in the 70-80° C. range, production of greater than 99% pBME and very little heavies formation was observed. An H$_2$S/PO mole ratio of 5:1 and PO WHSV of 0.75 h$^1$ also gave >99% pBME near 70° C. As emphasized by the linear trend lines, as more pBME is produced, more oxirane is consumed. Increased conversion of oxirane directly correlates to increased production of pBME (as indicated by the concentration of pBME in the reactor effluent).

TABLE 2

Summary of LZY-54 Conditions and Results

| | | Temp (° C.) | | | | |
|---|---|---|---|---|---|---|
| | | 40 | 50 | 60 | 70 | 80 |
| 0.5 WHSV | PO | 3.82 | 1.89 | 2.21 | 0.15 | 0 |
| 10:1 H2S ratio | pBME | 94.56 | 96.53 | 94.84 | 99.24 | 98.92 |
| | pBME-S | 0.45 | 0.8 | 2.08 | 0.55 | 0.37 |

TABLE 2-continued

Summary of LZY-54 Conditions and Results

| | | Temp (° C.) | | | | |
|---|---|---|---|---|---|---|
| | | 40 | 50 | 60 | 70 | 80 |
| | Conversion | 95.01 | 97.33 | 96.92 | 99.79 | 99.29 |
| | Selectivity | 99.53 | 99.18 | 97.85 | 99.45 | 99.63 |
| 0.5 WHSV | PO | 0.71 | 0.29 | 0.14 | 0 | |
| 5:1 H2S ratio | pBME | 98.61 | 99.53 | 97.91 | 98.33 | |
| | pBME-S | 0.63 | 0.18 | 1.94 | 1.67 | |
| | Conversion | 99.24 | 99.71 | 99.85 | 100 | |
| | Selectivity | 99.82 | 99.82 | 98.06 | 98.33 | |
| 0.75 WHSV | PO | | 0.77 | | 0 | 0 |
| 10:1 H2S ratio | pBME | | 97.65 | | 97.15 | 98.32 |
| | pBME-S | | 0.36 | | 2.82 | 1.62 |
| | Conversion | | 98.01 | | 99.97 | 99.94 |
| | Selectivity | | 99.63 | | 97.18 | 98.38 |
| 0.75 WHSV | PO | | 1.4 | 0.18 | 0.02 | |
| 5:1 H2S ratio | pBME | | 97.51 | 99.25 | 99.49 | |
| | pBME-S | | 1.08 | 0.47 | 0.49 | |
| | Conversion | | 98.59 | 99.72 | 99.98 | |
| | Selectivity | | 98.90 | 99.53 | 99.51 | |
| 1 WHSV | PO | | 1.7 | | | 0 |
| 10:1 H2S ratio | pBME | | 96.58 | | | 98.24 |
| | pBME-S | | 0.5 | | | 1.67 |
| | Conversion | | 97.08 | | | 99.91 |
| | Selectivity | | 99.48 | | | 98.33 |
| 1 WHSV | PO | | 1.79 | 0.79 | 0.04 | 0 |
| 5:1 H2S ratio | pBME | | 97.27 | 97.59 | 99.29 | 98.07 |
| | pBME-S | | 0.94 | 1.62 | 0.67 | 1.93 |
| | Conversion | | 98.21 | 99.21 | 99.96 | 100 |
| | Selectivity | | 99.04 | 98.37 | 99.33 | 98.07 |

This example shows that catalyst of alumina bound Y zeolite was superior to the catalysts in the previous examples. Reactor conditions were identified that allowed for more than 98% oxirane conversion while maintaining good reactor operability.

Figure 5:
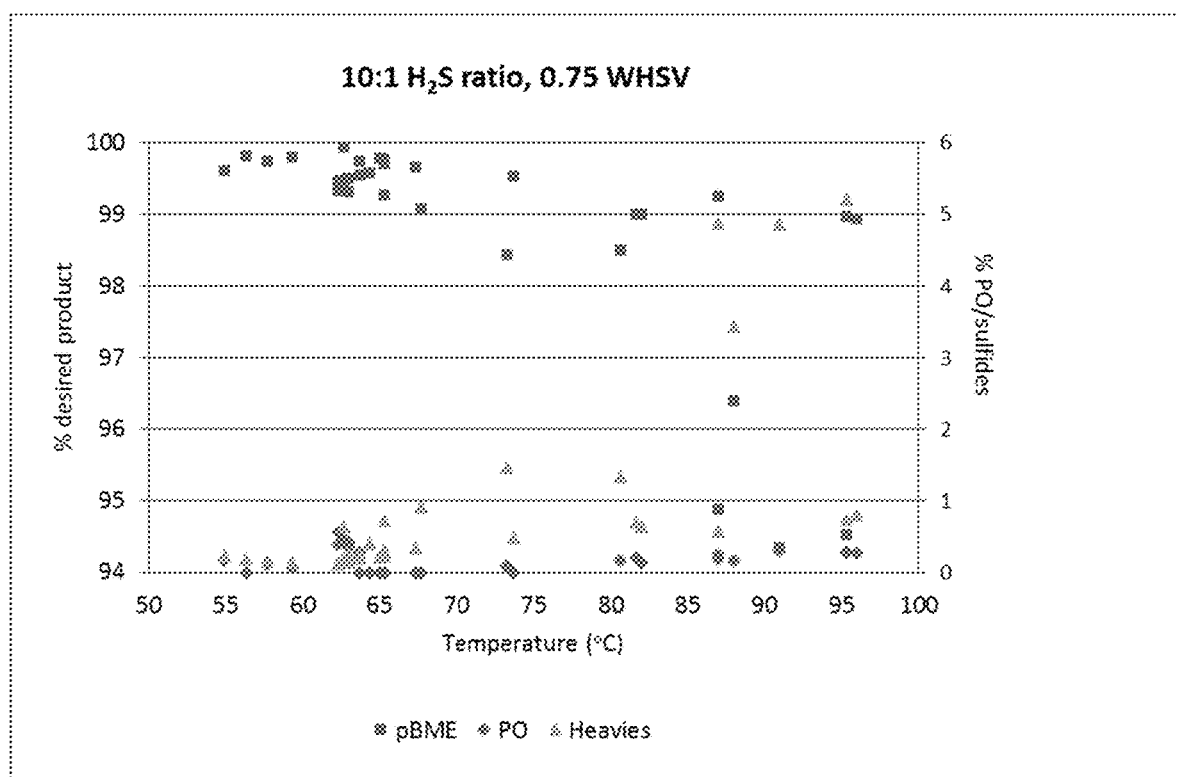
FIG. 5 is a chart of performance of LZY-64 zeolite.

The next series of experiments were performed with the LZY-64 catalyst and studied a variety of conditions for temperature, WHSV, and H$_2$S/PO ratio. The results summarized in Table 3 are averages of the individual experiments. Overall, the results indicate that LZY-64 is a more effective catalyst for the production of pBME when compared to the LZY-54 catalyst. A PO WHSV of 0.75 h$^1$ was optimal for this reaction: production was greater than or equal to 99% pBME and very little heavies formation was observed. The plot of desired product and starting material (PO) in FIG. 5 shows that controlling temperature between 55° to 80° C. resulted in a pBME product with greater than 99% (H$_2$S free) purity. The average conversion obtained from temperatures ranging from 60-85° C. was 99.4 with a standard deviation of 0.44. This example shows that this particular LZY-64 catalyst type of AS-Z catalyst made of Type Y zeolite was superior to the LZY-54 catalyst. Reactor conditions were identified that allowed for more than 99% oxirane conversion while maintaining good reactor operability.

TABLE 3

Summary of LZY-64 Conditions and Results

| LZY-64 | | Temp | | | |
|---|---|---|---|---|---|
| | | 50° C. | 60° C. | 70° C. | 80° C. |
| 0.5 WHSV | PO | 0.1 | 0.1 | 0.2 | 2.7 |
| 10:1 H2S ratio | pBME | 99.7 | 99.8 | 98.5 | 96.4 |
| | pBME-S | 0.2 | 0.1 | 1.3 | 1.0 |
| | Conversion | 99.9 | 99.9 | 99.8 | 97.4 |
| | Selectivity | 99.8 | 99.9 | 98.7 | 99.0 |

TABLE 3-continued

Summary of LZY-64 Conditions and Results

| LZY-64 | | Temp | | | |
|---|---|---|---|---|---|
| | | 50° C. | 60° C. | 70° C. | 80° C. |
| 0.75 WHSV | PO | 0.1 | 0.0 | 0.0 | 0.2 |
| 10:1 H2S ratio | pBME | 99.7 | 99.7 | 99.0 | 98.9 |
| | pBME-S | 0.2 | 0.3 | 1.0 | 0.9 |
| | Conversion | 99.9 | 100.0 | 100.0 | 99.8 |
| | Selectivity | 99.8 | 99.7 | 99.0 | 99.1 |
| 1 WHSV | PO | 0.0 | 0.0 | 0.2 | 4.1 |
| 10:1 H2S ratio | pBME | 99.8 | 99.8 | 98.4 | 97.9 |
| | pBME-S | 0.2 | 0.2 | 1.4 | 1.9 |
| | Conversion | 100.0 | 100.0 | 99.8 | 99.8 |
| | Selectivity | 99.8 | 99.8 | 98.6 | 98.1 |

Select experiments were repeated similarly as described above, except ethylene oxide was used as the reactant. In the case of LZY-64 catalyst, the catalyst bed was first diluted with Alundum such that 30% (by volume) of the top of the bed was catalyst, 50% (by volume) of the middle of the bed was catalyst, and 100% (by volume) of the bottom of the bed was catalyst. While the heat of reaction was difficult to control in this catalyst configuration, these conditions did demonstrate excellent selectivity toward BME. At a 0.2 WHSV ratio, pressure of 450 psig, and a 45:1 mol ratio of $H_2S$ to EO, the reaction exotherm was kept under 70° C.; however, when the mol ratio was decreased to 30:1, the exotherm increased to 94° C. Because operating at a 45:1 mol ratio is not practical at plant-scale, the catalyst bed was repacked at a higher dilution.

Subsequent tests of the LZY-64 catalyst using a dilution of 15%/15%/50% by volume of catalyst in the top, middle, and bottom beds, respectively, also showed good selectivity toward BME (>99%), even at temperatures exceeding 100° C., but high $H_2S$ ratios were required. The results of the LZY-64 experiments using EO at both catalyst bed configurations are shown in Table 4 below.

In an attempt to better control the heat of reaction, a catalyst bed was designed using LZY-54 at percentages (by volume) of 30%/50%/100% in the top, middle, and bottom portions of the bed, respectively. At a mol ratio of 40:1, >99% pure BME was produced at WHSVs of 0.3 and less and a pressure of 450 psig. Table 5 below shows the results of the experiments using the LZY-54 catalyst with EO The LZY-64 catalyst using the 15%/15%/50% packing design as described previously was then evaluated at a higher pressure (650 psig) in an effort to further control the heat of reaction (at 650 psig, $H_2S$ is a liquid). Good temperature control was achieved at $H_2S$ mol ratios as low as 12:1 and a WHSV as high as 0.50. For comparative purposes, the LZY-54 catalyst bed with the 30%/50%/100% packing design was also tested. The exotherm was slightly more difficult to control; however, this is likely due to the fact that the bed contained less diluent by volume. In the case of the LZY-54 bed, as the $H_2S$ ratio increased, the purity of the BME product also increased. The performance of both catalysts at 450 psig are shown in Tables 4 and 5 below.

TABLE 4

LZY-64 Catalyst tested with Ethylene Oxide

| Catalyst Bed (vol %) | WHSV | H2S Ratio | Rx psig | Temperature (° C.) | | | GC Results % BME |
|---|---|---|---|---|---|---|---|
| | | | | Top zone | Mid zone | Btm zone | |
| 30/50/100 | 0.20 | 45:1 | 440-450 | 45 | 64 | 63 | 100 |
| 30/50/100 | 0.20 | 30:1 | 440-450 | 49 | 94 | 62 | 99.6 |
| 15/15/50 | 0.50 | 30:1 | 440-450 | 58 | 75 | 57 | 99.9 |
| 15/15/50 | 1.00 | 30:1 | 440-450 | 52 | 101 | 91 | 99.1 |
| 15/15/50 | 0.30 | 30:1 | 440-450 | 63 | 63 | 53 | 99.5 |
| 15/15/50 | 0.30 | 30:1 | 440-450 | 103 | 56 | 36 | 99.9 |
| 15/15/50 | 0.40 | 12:1 | 650 | 60 | 55 | 55 | 99.8 |
| 15/15/50 | 0.50 | 15:1 | 650 | 59 | 54 | 52 | 99.2 |
| 15/15/50 | 0.40 | 15:1 | 650 | 57 | 54 | 53 | 99.4 |
| 15/15/50 | 0.30 | 20:1 | 650 | 64 | 55 | 54 | 99.3 |

TABLE 5

LZY-54 Catalyst tested with Ethylene Oxide

| Catalyst Bed (vol %) | WHSV | H2S Ratio | Rx psig | Temperature (° C.) | | | GC Results % BME |
|---|---|---|---|---|---|---|---|
| | | | | Top zone | Mid zone | Btm zone | |
| 30/50/100 | 0.30 | 40:1 | 440-450 | 33 | 54 | 79 | 99.8 |
| 30/50/100 | 0.20 | 40:1 | 440-450 | 33 | 60 | 70 | 99.9 |
| 30/50/100 | 0.40 | 20:1 | 650 | 60 | 65 | 38 | 99.5 |
| 30/50/100 | 0.40 | 15:1 | 650 | 68 | 70 | 43 | 99.2 |
| 30/50/100 | 0.40 | 12:1 | 650 | 53 | 67 | 47 | 98.8 | pH Testing

Acidic characteristics of the catalysts were investigated by measuring the change in the pH level of a water sample occurring after immersion of the catalyst. The studies were conducted in round-bottomed flasks with continuous stirring at a constant temperature of 30° C. Studies were conducted with the catalysts as received as well as with water-rinsed forms of the catalysts. In each pH study, a 10x weight of water was used as compared to catalyst weight. The initial pH of the water was measured then the catalyst was added and stirred for 2 h at 30° C. before measuring the final pH of the water. Water-rinsing of the catalysts was performed by placing the catalyst in a column and washing with 15x volumes of water, then drying at 70° C. prior to conducting the pH study. The results of the pH study are shown in in Table 6. The 13X molecular sieves (Type X zeolite) and the LEWATIT® MP-62 are both are known to be basic, so it is not surprising that these catalysts caused the pH to increase. The 13X molecular sieves did not achieve the best conversion and selectivity with respect to BME, it produced heavies that plugged the reactor, and it deactivated over time, likely due to elevated temperatures. The LEWATIT® MP-62 did perform well, achieving very good conversion and selectivity with respect to BME. However, this catalyst does cause a very significant increase in pH which may not always be desirable in industrial practice. LEWATIT® MP-62 comprises an amine supported on polystyrene. At pH values above about 9, amine desorbs and interacts with metals such as iron that may be present. From a manufacturing standpoint, it may not be desirable to have trace amounts of amines and/or metals in the final product, especially if the BME being produced needs to be very high purity, as removing these impurities would require one or more additional process steps. Additionally, the LEWATIT® MP-62 has a very small particle size, which can cause handling and pressure drop issues, and the polystyrene support is very sensitive to temperature spikes.

AMBERLYST® 15 is known to be acidic, and as expected, decreased the pH. While this reaction can proceed with acidic catalysts, if the pH is too low (as in the case of AMBERLYST® 15), conditions favor production of polymeric molecules (such as polymeric thioethers) that plug up the reactor bed.

LZY-54 and LZY-64, which are both Type Y zeolites, are considered to be mildly acidic catalysts; however, in the presence of water, the two catalysts exhibit very different pH effects. As shown by the pH data below, in the presence of water LZY-54 causes a larger pHincrease than the LZY-64. LZY-54 creates basic pH conditions while LZY-64 maintains neutral or very slightly acidic conditions. This difference is explained by the fact that the LZY-54 is a Na—Y type zeolite and the LZY-64 is the protonated form H-Y zeolite. In the LZY-64, the Na+ is exchanged with NH$_4$+ followed by washing and calcination at high temperature to drive out NH$_3$, creating a purely protonated form of the zeolite, which in turn creates a mildly acidic pH effect in water. It is surprising that the exchange of one ion for another on the zeolite can have such a significant effect on the outcome of this reaction. One of ordinary skill in the art would expect the LZY-54 and LZY-64 catalysts to produce very similar results, and in fact, up to conversions of about 98 wt. %, they do. However, the data clearly shows that the LZY-64 produces optimum conversion, selectivity, and purity results at the preferred reactor operating conditions. The results of these experiments have unexpectedly shown that the degree of acidity and magnitude of the pH change caused by the catalyst are quite important when it comes to maximizing conversion and selectivity and minimizing formation of undesired byproducts, especially when the desired conversion and purity are >99 wt. %. It is also surprising that the LZY-54 and LZY-64 catalysts both produce very little heavy impurities compared to the other catalysts, especially considering the LZY-64 is slightly acidic, which typically favors formation of heavies. Additionally, while the LZY-64 performs comparably to the LEWATIT® MP-62 with respect to conversion and selectivity, use of LZY-64 allows the reactor to operate at a much more moderate (i.e., neutral) pH range that will prevent the product from having any trace amine or metal impurities, and LZY-64 is much more tolerant of temperature spikes. Finally, and contrary to what one of ordinary skill in the art might expect, acidic-type catalysts do not all perform the same for this application. The data presented here clearly shows that catalysts with similar properties cannot simply be interchanged in a BME synthesis process with the expectation that the results will be the same or comparable. The results shown here demonstrate the ability to produce very high purity (>99 wt. %) BME that requires no other separation and/or purification steps other than the removal of H$_2$S, which is critical to the economic viability of this process.

TABLE 6 pH Effects, Composition, and Performance of Catalysts

| Catalyst | As Received | | | Pre-Rinsed | | | Si/Al molar ratio | Performance in PFR Reactor with PO and H$_2$S |
|---|---|---|---|---|---|---|---|---|
| | Initial pH | Final pH | Δ pH | Initial pH | Final pH | Δ pH | | |
| LZY-64* | 6.06 | 6.27 | −0.21 | 5.87 | 5.79 | 0.08 | 2.17 | >99% conversion and excellent selectivity |
| LZY-54* | 6.11 | 8.52 | −2.41 | 5.86 | 9.04 | −3.18 | 2.60 | High conversion and excellent selectivity |
| 13X Mol. Sieve* | 6.04 | 10.67 | −4.63 | 5.94 | 10.3 | −4.36 | 1.4 ± 0.1 | Good conversion; Catalyst became deactivated |
| Amberlyst ® 15† | 5.8 | 1.95 | 3.85 | 6.14 | 2.1 | 4.08 | N/A | Reactor became plugged |
| Lewatit ® MP-62‡ | 6.05 | 9.28 | −3.23 | 6.26 | 9.18 | −2.92 | N/A | Good conversion |
| Lewatit ® K 2620† | Not part of pH study | | | | | | N/A | Reactor became plugged |

*Aluminosilicate zeolite
†Stryene-divinylbenzene copolymer resin
‡Anion exchange resin functionalized with tertiary amine groups
*Acid-treated clay
pH Change    Aidic    Basic Additional Disclosure Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

We claim:
1. A process comprising:
   introducing hydrogen sulfide and ethylene oxide into a plug flow reactor having a fixed bed containing a solid catalyst comprising LZY-64 catalyst;
   reacting the hydrogen sulfide and the ethylene oxide in the presence of the solid catalyst to yield a reaction product comprising 2-mercapto-1-ethanol (beta-mercaptoethanol), wherein during a steady state operation of the plug flow reactor, the hydrogen sulfide and the ethylene oxide are introduced in a mole ratio in a range of about 5:1 to about 50:1, wherein after a single pass through the plug flow reactor, a conversion of the ethylene oxide to 2-mercapto-1-ethanol is greater than 99 wt %, and wherein conversion is calculated by dividing a weight of the ethylene oxide that is converted to 2-mercapto-1-ethanol by a weight of the ethylene oxide fed to the plug flow reactor.

2. The process of claim 1, wherein the reaction product further comprises equal to or less than about 6 wt. % thiodiglycol on a hydrogen sulfide-free basis.

3. The process of claim 1, wherein the reaction product further comprises equal to or less than about 1.5 wt. % thiodiglycol on a hydrogen sulfide-free basis.

4. The process of claim 1, wherein the reaction product further comprises equal to or less than about 0.5 wt. % thiodiglycol on a hydrogen sulfide-free basis.

5. The process of claim 1, wherein the LZY-64 catalyst is an aluminosilicate Type Y zeolite having acidic active groups comprising Brønsted acid sites and Lewis acid sites.

6. The process of claim 1, wherein the solid catalyst comprises a molar ratio of Si to Al in a range of from about 2.1:1 to about 2.7:1.

7. The process of claim 1, wherein a weight hourly space velocity of the ethylene oxide is in a range of from about 0.2 to about 2.0 h$^{-1}$, wherein an amount of thiodiglycol in an effluent of the plug flow reactor comprises less than about 1 wt. % on a hydrogen sulfide-free basis.

8. The process of claim 1, further comprising:

converting, in the plug flow reactor, at least a portion of the hydrogen sulfide from a liquid phase to a vapor phase to absorb a heat of reaction created in the step of reacting.

9. The process of claim 1, wherein the plug flow reactor is adiabatic and no internal and/or external cooling source is used to cool the plug flow reactor.

10. The process of claim 1, wherein 0.1 wt. % or less ethanedithiol is present in the reaction product on a hydrogen sulfide free basis.

11. The process of claim 1, performed at a temperature in a range of about 30° C. to about 100° C.

12. The process of claim 1, wherein the fixed bed of the plug flow reactor has a weight average bed temperature of about 50° C. to about 80° C.

13. The process of claim 1, performed at a pressure in a range of about 400 psig to about 750 psig.

14. The process of claim 1, further comprising:

recovering a vapor phase of the hydrogen sulfide from the plug flow reactor;

condensing the vapor phase of the hydrogen sulfide to a liquid phase; and recycling the liquid phase of the hydrogen sulfide to the plug flow reactor.

15. The process of claim 1, wherein the reaction product leaving the plug flow reactor is comprised of 99.0 wt. % or greater 2-mercapto-1-ethanol on a hydrogen sulfide free basis.

16. The process of claim 1, wherein a product conversion of ethylene oxide to reaction product is 99.0 wt. % or greater and the product conversion is achieved in a single pass of ethylene oxide through the plug flow reactor, and wherein the product conversion is calculated by dividing a weight of the ethylene oxide that is converted to all reaction products by a weight of the ethylene oxide fed to the plug flow reactor.

17. The process of claim 1, wherein a product conversion of ethylene oxide to reaction product is 99.5 wt. % or greater and the product conversion is achieved in a single pass of ethylene oxide through the plug flow reactor, and wherein the product conversion is calculated by dividing a weight of the ethylene oxide that is converted to all reaction products by a weight of the ethylene oxide fed to the plug flow reactor.

18. The process of claim 1, wherein a product conversion of ethylene oxide to reaction product is 99.9 wt. % or greater and the product conversion is achieved in a single pass of ethylene oxide through the plug flow reactor, and wherein the product conversion is calculated by dividing a weight of the ethylene oxide that is converted to all reaction products by a weight of the ethylene oxide fed to the plug flow reactor.

19. A reactor system for producing 2-mercapto-1-ethanol, comprising:

a plug flow reactor;

an ethylene oxide stream coupled to the plug flow reactor and configured to feed ethylene oxide to the plus flow reactor;

a hydrogen sulfide stream coupled to the plug flow reactor and configured to feed hydrogen sulfide to the plug flow reactor;

a fixed bed containing a solid zeolite catalyst in the plug flow reactor, wherein the solid zeolite catalyst comprises LZY-64 catalyst; and an effluent stream connected to the plug flow reactor, wherein the effluent stream comprises 2-mercapto-1-ethanol, wherein the reactor system is configured such that after a single pass through the plug flow reactor, a conversion of the ethylene oxide to 2-mercapto-1-ethanol is greater than 99.0 wt. %, wherein conversion is calculated by dividing a weight of the ethylene oxide that is converted to 2-mercapto-1-ethanol by a weight of the ethylene oxide fed to the plug flow reactor.

20. The reactor system of claim 19, wherein the plug flow reactor is adiabatic and the reactor system includes no internal and/or external source for cooling the plug flow reactor.

21. The reactor system of claim 19, wherein the fixed bed of the solid zeolite catalyst comprises a top zone, a middle zone, and a bottom zone; and wherein the top zone includes from about 66% to about 90% of a chemically inert solid diluent and about 15% to about 33% solid zeolite catalyst by volume, the middle zone includes about at least about 50% to about 90% of the chemically inert solid diluent and up to about 10% to about 50% solid zeolite catalyst, and the bottom zone includes up to 100% solid zeolite catalyst by volume.

22. The reactor system of claim 19, wherein the LZY-64 catalyst is an aluminosilicate zeolite Type Y zeolite having acidic active groups comprising Brønsted acid sites and Lewis acid sites.

23. The reactor system of claim 19, wherein the effluent stream further comprises less than about 3 wt. % thiodiglycol on a hydrogen sulfide free basis.

24. The reactor system of claim 19, wherein the effluent stream comprises less than 0.1 wt. % ethanedithiol on a hydrogen sulfide free basis.

25. The reactor system of claim 19, wherein the ethylene oxide stream and the hydrogen sulfide stream each connect directly to the plug flow reactor without mixing ethylene oxide and hydrogen sulfide prior to introduction to the plug flow reactor.

26. The reactor system of claim 25, wherein a temperature measuring device comprising a thermocouple or resistance temperature detector is placed in an end of the ethylene oxide stream which is connected to the plug flow reactor, wherein the temperature measuring device is linked to a controller configured to stop a flow of the ethylene oxide stream upon detecting a temperature in the ethylene oxide stream which is above a threshold temperature.

27. The reactor system of claim 19, wherein the ethylene oxide stream and the hydrogen sulfide stream are each connected to a mixing stream and the mixing stream is connected to the plug flow reactor.

28. The reactor system of claim 27, wherein a temperature measuring device comprising a thermocouple or resistance temperature detector is placed in an end of the mixing stream which is connected to the plug flow reactor, wherein the temperature measuring device is linked to a controller configured to stop a flow of the ethylene oxide stream upon detecting a temperature in the mixing stream which is above a threshold temperature.

29. The reactor system of claim 19, wherein the hydrogen sulfide stream is coupled to the plug flow reactor such that hydrogen sulfide is fed to the plug flow reactor in a down-flow orientation.

30. A process comprising:
reacting, in a plug flow reactor having a fixed bed containing a solid catalyst comprising LZY-64 catalyst, hydrogen sulfide and an oxirane compound in the presence of the solid catalyst to yield a reaction product comprising a mercapto-alcohol, wherein the mercapto-alcohol comprises 2-mercapto-1-ethanol or 1-mercapto-2-propanol, wherein during steady state operation of the plug flow reactor, the hydrogen sulfide and the oxirane are present in a mole ratio in a range of about 5:1 to about 50:1, wherein an effluent of the plus flow reactor comprises the reaction product, wherein after a single pass through the plug flow reactor a conversion of the oxirane to 2-mercapto-1-ethanol or 1-mercapto-2-propanol is greater than 99 wt. %, and wherein the conversion of the oxirane compound to 2-mercapto-1-ethanol or 1-mercapto-2-propanol is based on a weight of the oxirane compound that converts to 2-mercapto-1-ethanol or 1-mercapto-2-propanol divided by a weight of the oxirane compound fed to the plug flow reactor.

31. The process of claim 30 wherein the oxirane compound is ethylene oxide and the mercapto-alcohol is 2-mercapto-1-ethanol.

32. The process of claim 30 wherein the oxirane compound is propylene oxide and the mercapto-alcohol includes 1-mercapto-2-propanol.

33. The process of claim 32 wherein the mercapto-alcohol further includes 2-mercapto-1-propanol.

34. The process of claim 30, wherein the fixed bed of the plug flow reactor has a weight average bed temperature of about 50° C. to about 80° C.

35. The process of claim 30, performed at a pressure in a range of about 400 psig to about 750 psig.

36. The process of claim 30, wherein a weight hourly space velocity of the oxirane is in a range of from about 0.2 to about 2.0 $h^{-1}$.

37. The process of claim 30, wherein a selectivity to the mercapto-alcohol is greater than about 99.0 wt. % based on a total weight of the oxirane that was converted to the mercapto-alcohol divided by a total weight of the oxirane that was converted into the reaction product.

* * * * *